US008623649B2

(12) United States Patent
Hattori et al.

(10) Patent No.: US 8,623,649 B2
(45) Date of Patent: Jan. 7, 2014

(54) METHOD OF SELECTING A CARDIOMYOCTYE USING INTRACELLULAR MITOCHONDRIA AS AN INDICATOR

(75) Inventors: Fumiyuki Hattori, Tokyo (JP); Keiichi Fukuda, Tokyo (JP)

(73) Assignees: Daiichi Sankyo Company, Limited, Tokyo (JP); Keio University, Tokyo (JP)

( * ) Notice: Subject to any disclaimer, the term of this patent is extended or adjusted under 35 U.S.C. 154(b) by 1503 days.

(21) Appl. No.: 11/660,581

(22) PCT Filed: Aug. 26, 2005

(86) PCT No.: PCT/JP2005/015553
§ 371 (c)(1),
(2), (4) Date: Sep. 19, 2007

(87) PCT Pub. No.: WO2006/022377
PCT Pub. Date: Mar. 2, 2006

(65) Prior Publication Data
US 2008/0090266 A1    Apr. 17, 2008

(30) Foreign Application Priority Data

Aug. 27, 2004 (JP) ................................ 2004-247785
Jul. 15, 2005 (JP) ................................ 2005-207799

(51) Int. Cl.
*A61K 35/34* (2006.01)

(52) U.S. Cl.
USPC ............ 435/378; 435/366; 435/363; 435/352

(58) Field of Classification Search
None
See application file for complete search history.

(56) References Cited

FOREIGN PATENT DOCUMENTS

JP            10-253622        9/1998

OTHER PUBLICATIONS

Chen, L.B. "Mitochondrial Membrane Potential in Living Cells" Annual Review of Cell Biology, 1988 vol. 4, 155-181.*
Barth et al, "Ultrastructural quantitation of mitochondria and myofilaments in cardiac muscle from 10 different animal species including man." Journal of Molecular and Cellular Cardiology, vol. 24 Issue 7, 1992, 669-681.*
Lampidis et al. "Rhodamine-123 is Selectively Toxic and Preferentially Retained in Carcinoma Cells In Vitro." Annals New York Academy of Sciences, vol. 397, 1982, 299-302.*
Haugland, R.P., "Handbook of Fluorescent Probes and Research Products; Chapter 12—Probes for Organelles; Section 12.2—Probes for Mitochondria" Molecular Probes, Inc. Ninth Edition, 2002, 473-488.*
Boheler "Differentiation of Pluripotent Embryonic Stem Cells into Cardiomyocytes" Circulation Research, 2002, vol. 91 189-201.*

(Continued)

*Primary Examiner* — Jon P Weber
*Assistant Examiner* — Charles Zoltan Constantine
(74) *Attorney, Agent, or Firm* — Hunton & Williams LLP

(57) ABSTRACT

The invention relates to methods of selecting a cardiomyocyte from a cell population derived from a whole heart or a differentiated cell population derived from a stem cell without genetic alteration. Specifically, the invention relates to a method of selecting a cardiomyocyte from a cardiomyocyte-containing cell mixture without genetic alteration of a cardiomyocyte, on the basis of a relative content of cellular mitochondria and/or a relative mitochondrial transmembrane potential of the cell. The invention also relates to methods of enriching a cardiomyocyte from a cardiomyocyte-containing cell mixture without genetic alteration of a cardiomyocyte, producing a cardiomyocyte without genetic alteration of a cardiomyocyte, and evaluating the ratio of a cardiomyocyte in a cardiomyocyte-containing cell mixture.

26 Claims, 16 Drawing Sheets

Isolation based on ES Cell-Derived Cardiomyocytes Labeled with M7152

(56) References Cited

OTHER PUBLICATIONS

Mathur A. et al., "Evaluation of Fluoresecent dyes for the detection of mitochondrial membrane potential changes in cultured cardiomyocytes", Cardiovascular Research, 2000, vol. 46, pp. 126-138.

Swift L. M. et al., "Localization of dichlorofluorescin in cardiac myocytes: implications for assessment of oxidative Stress", Am. J. Physiol. Heart Circ. Physiol., 2000, vol. 278, pp. H982-H990.

Fukuda K. et al., "Regeneration of Cardiomyocytes from bone marrow: Use of mesenchymal stem cell for cardiovascular tissue engineering", Cytotechnology, 2003, vol. 41, pp. 165-175.

Muller M. et al., "Selection of ventricular-like cardiomyocytes from ES cells in vitro.", The FASEB Journal, 2000, vol. 14, pp. 2540-2548.

Else P. L. et al., "Mammals: an allometric study of metabolism at tissue and mitochondrial level", American Journal of Physiology, 1985, vol. 248, pp. R415-R421.

Summerhayes I. C., et al., "Unusual retention of rhodamine 123 by mitochondria in muscle and carcinmoa cells", Proc. Natl. Acad. Sci. USA, 1982, vol. 79, pp. 5292-5296.

Fijnvandraat A. C. et al., "Cardiomyocytes purified from differentialtied embryonic stem cells exhibit characteristics of early chamber myocardium", Journal of Molecular and Cellular Cardiology, 2003, vol. 35, pp. 1461-1472.

Rottenberg H. et al., "Quantitative assay by flow cytometry of the mitochondrial membrane potential in intact cells", Biochmia et Biophysica Acta, 1998, vol. 1404, pp. 393-404.

M. Müller, et al., "Selection of Ventricular-like Cardiomyocytes from ES cells in vitro", The FASEB Journal, vol. 14, p. 2540-2548, Dec. 2000.

M. Klug, et al., "Genetically Selected Cardiomyocytes from Differentiating Embryonic Stem Cells Form Stable Intracardiac Grafts", J. Clin. Invest., vol. 98, No. 1, p. 216-224, Jul. 1996.

P. L. Else, et al., "Mammals: An allometric study of Metabolism at Tissue and Mitochondrial Level", Am. J. Physiol., p. R415-R421, 1985.

Chunhui Xu, et al., "Characterization and Enrichment of Cardiomyocytes Derived from Human Embryonic Stem Cells", Circ. Res., vol. 91, p. 501-508, 2002.

Kyoko Hidaka, et al., "Chamber-Specific Differentiation of Nkx2.5-positive Cardiac Precursor Cells from Murine Embryonic Stem Cells", The FASEB Journal, Published online on Feb. 19, 2003.

A. Fijnvandraat, et al., "Cardiomyocytes Purified from Differentiated Embryonic Stem Cells exhibit Characteristics of early Chamber Myocardium", Journal of Molecular and Cellular Cardiology, vol. 35, p. 1461-1472, 2003.

Natig Gassanov, et al., "Endothelin induces Differentiation of ANP-EGFP expressing embryonic stem cells towards a pacemaker phenotype", The FASEB Journal, p. 1-19, Published online on Sep. 2, 2004.

Ichinose, et al. (2003) "Diazoxide triggers cardioprotection against oxidative stress." *Am J Phisool Heart Circ Physiol* 284: H2235-2241.

\* cited by examiner

Comparison of M7512 Fluorescent Intensity between Primary Cardiomyocytes and Non-Cardiomyocytes.

Fluorescent Intensity Analysis of Whole Heart Constituting Cell Population Labeled with M7512 Derived from Neonatal Rats

Staining with Actinin, Myocardial Marker, of High Fluorescent Cell Population (P2) Isolated from M7512 Labeled ES Cells

| High T668 Fluorescent Cell Population | Middle T668 Fluorescent Cell Population |
|---|---|
| Actinin Immunostaining | Actinin Immunostaining |
| 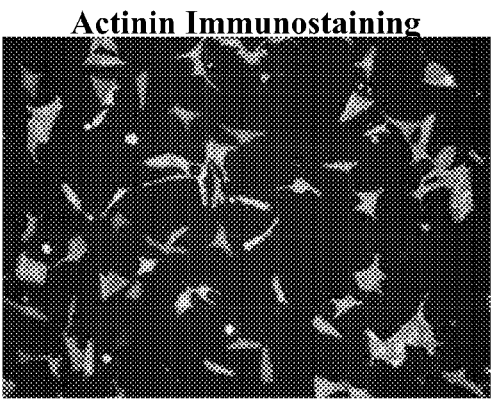 | 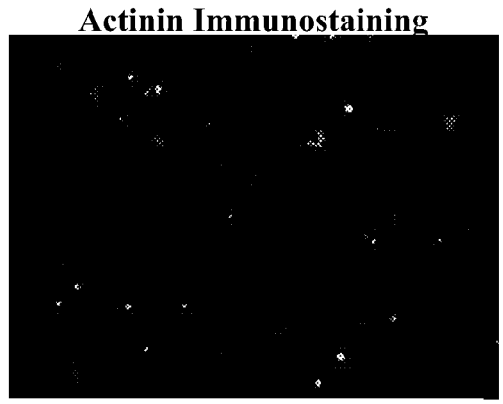 |
| Phase-Contrast Image | Phase-Contrast Image |
| 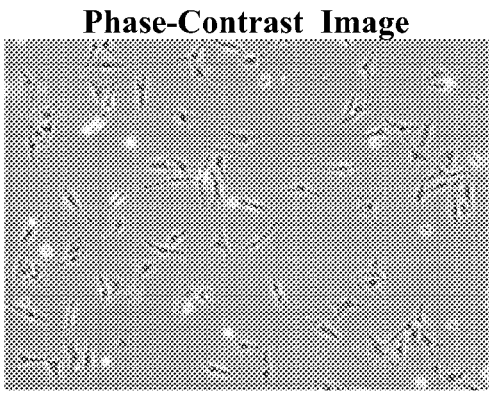 | 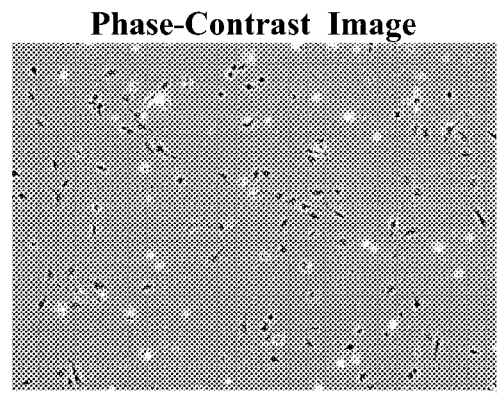 |
FIGURE 8-2

High Fluorescent Cell Population
Actinin Immunostaining
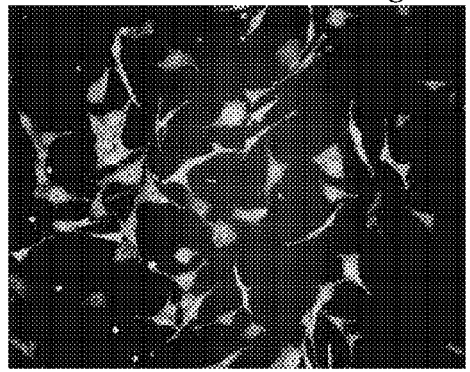
Middle Fluorescent Cell Population
Actinin Immunostaining
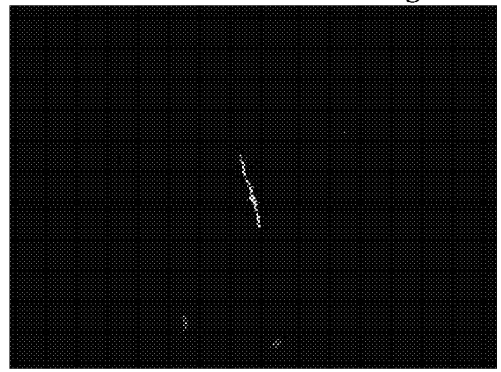
Phase-Contrast Image
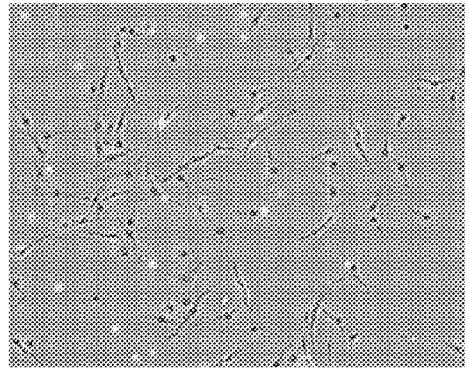
Phase-Contrast Image
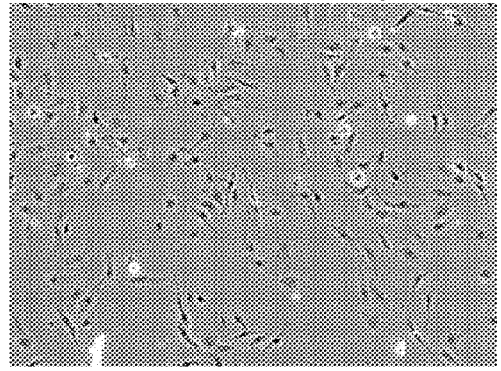
FIGURE 9-2

METHOD OF SELECTING A CARDIOMYOCTYE USING INTRACELLULAR MITOCHONDRIA AS AN INDICATOR

CROSS-REFERENCE TO RELATED APPLICATIONS

This application is a U.S. national stage application of International Application No. PCT/JP2005/015553, filed on Aug. 26, 2005, which claims the benefit of Japanese Application Serial No. 2004-247745, filed on Aug. 27, 2004, and Japanese Application Serial No. 2005-207799, filed Jul. 15, 2005, the disclosures of each of which are herein incorporated by reference in their entireties.

BACKGROUND OF THE INVENTION (i) Field of the Invention
(ii) Description of the Related Art Since a cardiomyocyte loses a proliferative ability in an adult body, it is necessary to conduct cardiac transplantation in treating a serious heart disease such as cardiac infarction or cardiomyopathy. However, currently, since insufficient donor hearts are available, there is now a pressing need to develop a method of treatment other than cardiac transplantation. On the other hand, the recruitment of the ex vivo produced cardiomyocyte is expected to be a most promising method of providing relief for patients in need of cardiac transplantation.

Various methods of preparing a cardiomyocyte have been investigated, such as a method of using a differentiated embryonic stem cell, a method of inducing and differentiating a stem cell (somatic stem cell) isolated from a living body that is suggested to be within the body, and so on. However, there is a problem in the art that, it is in the nature of a stem cell that cells other than a cardiomyocyte are always developed from the stem cell as a by-product during the differentiation/induction procedure and that an undifferentiated stem cell always remains even after the differentiation/induction procedure. Thus, it has been considered in the art that the differentiated/induced cell population itself can not be used in the treatment method. Therefore, it is necessary to select a cardiomyocyte from the differentiated/induced cell population in order to successfully achieve cardiac transplantation in a human.

To date, an effective method of purifying a cardiomyocyte is not reported in the art other than a method of purifying a cardiomyocyte by incorporating in advance a marker gene into genome of the stem cell (FASEB J., 2000, 14: 2540-2548). However, since alteration of genome includes intrinsic ethical concerns and involves unpredictable serious risks including changes in the rate of malignant alteration, alteration of genome for practical use in a human raises significant questions.

It is known in the art that myocardial oxygen demand is relatively higher than that of major tissues other than heart and that the content of myocardial mitochondria is also relatively higher than that of other tissue (Am. J. Physiol., 1985, 248: R415-421). Further, it is well known in the art that a cardiomyocyte seriously loses mitotic capacity once the cell has differentiated and matured. However, it was not previously known at all that those ordinarily skilled in the art had tried to select a cardiomyocyte by applying the characteristics of the cardiomyocyte described above. Further, there was no report of directly comparing a mitochondrial transmembrane potential of the cardiomyocyte with mitochondrial transmembrane potential of other types of cells, of focusing on the mitochondrial transmembrane potential, and of selecting the cardiomyocyte using mitochondrial transmembrane potential as an indicator of the cardiomyocyte.

[non-patent document 1] FASEB J., 2000, 14: 2540-2548
[non-patent document 2] Am. J. Physiol., 1985, 248:R415-421

SUMMARY OF THE INVENTION

The present inventors set out to solve a problem of developing a method of selecting a cardiomyocyte without genetic alteration from a cell mixture derived from a whole heart and cell mixture derived from a cell having an ability to differentiate to the cardiomyocyte using various kinds of properties of the cardiomyocyte, which is not directly linked with selection of the cardiomyocyte.

The present inventors successfully solved the problem described above on the basis of the findings that the cardiomyocyte contains relatively higher amount of mitochondria than any other types of cells, and that mitochondria of the cardiomyocyte has relatively higher transmembrane potential than any other types of cells. Based on these findings, the present inventors established an innovative method of selecting a cardiomyocyte without genetic alteration of the cardiomyocyte, which comprises the following steps: a step of labeling a cardiomyocyte-containing cell mixture using a mitochondria specific labeling reagent, and a step of measuring a relative content of cellular mitochondria and/or mitochondrial transmembrane potential.

Specifically, in the first embodiment, the present invention provides a method of selecting a cardiomyocyte from a cardiomyocyte-containing cell mixture without genetic alteration of the cardiomyocyte, on the basis of a relative content of cellular mitochondria and/or a relative mitochondrial transmembrane potential of the cell.

That is to say, in the first embodiment, the present invention provides:
a method of selecting a cardiomyocyte from a cardiomyocyte-containing cell mixture without genetic alteration of the cardiomyocyte, on the basis of a relative content of cellular mitochondria;
a method of selecting a cardiomyocyte from a cardiomyocyte-containing cell mixture without genetic alteration of the cardiomyocyte, on the basis of both of a relative mitochondrial transmembrane potential of the cell; or
a method of selecting a cardiomyocyte from cardiomyocyte-containing cell mixture without genetic alteration of the cardiomyocyte, on the basis of a relative content of cellular mitochondria and transmembrane potential.

This embodiment of the method of the present invention is characterized by the steps of labeling a cardiomyocyte-containing cell mixture with a mitochondrial indicator, and of measuring a relative content of cellular mitochondria and/or a relative mitochondrial transmembrane potential of the cell.

In the context of the invention, the cardiomyocyte-containing cell mixture may be a cell mixture derived from a whole heart or a cell mixture derived from a cell having an ability to differentiate to a cardiomyocyte.

Further, a cell having an ability to differentiate to a cardiomyocyte may be selected from the group consisting of a stem cell, a progenitor cell and an egg cell.

In this embodiment, after the step of labeling a cardiomyocyte-containing cell mixture with a mitochondrial indicator and before the step of measuring a relative content of cellular mitochondria and/or a relative mitochondrial transmembrane potential of the cell, the method of the present invention may further comprise a step of culturing the labeled cell in the absence of the mitochondrial indicator.

Moreover, the mitochondrial indicator used in this embodiment of the present invention may be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment, M7512, T3168, T668 or R302 are preferable as a mitochondrial indicator.

In the second embodiment, the present invention provides a method of enriching a cardiomyocyte from a cardiomyocyte-containing cell mixture without genetic alteration of the cardiomyocyte, wherein said method comprises the following steps:
  (1) a step of labeling the cardiomyocyte-containing cell mixture with a mitochondrial indicator; and
  (2) a step of selecting the cardiomyocyte on the basis of a relative content of cellular mitochondria and/or a relative mitochondrial transmembrane potential of the cell.

In the context of the second embodiment of the present invention, the cardiomyocyte-containing cell mixture may be a cell mixture derived from a whole heart or a cell mixture derived from a cell having an ability to differentiate to the cardiomyocyte.

Further, a cell having an ability to differentiate to a cardiomyocyte may be selected from the group consisting of a stem cell, a progenitor cell and an egg cell.

In the second embodiment, after the step (1) and before the step (2), the method of the present invention may further comprise a step of culturing the labeled cell in the absence of the mitochondrial indicator.

Moreover, the mitochondrial indicator used in this embodiment of the present invention may be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment, M7512, T3168, T668 or R302 are preferable as a mitochondrial indicator.

In the third embodiment, the present invention provides a method of producing a cardiomyocyte without genetic alteration of the cardiomyocyte, wherein said method comprises the following steps:
  (1) a step of differentiating and inducing the cardiomyocyte from a cell having an ability to differentiate to the cardiomyocyte to prepare a cardiomyocyte-containing cell mixture;
  (2) a step of labeling the cardiomyocyte-containing cell mixture with a mitochondrial indicator; and
  (3) a step of selecting the cardiomyocyte on the basis of a relative content of cellular mitochondria and/or a relative mitochondrial transmembrane potential of the cell.

In the context of the third embodiment of the present invention, a cell having an ability to differentiate to the cardiomyocyte may be selected from the group consisting of a stem cell, a progenitor cell and an egg cell.

In addition, after the step (2) and before the step (3), the method of the present invention may further comprise a step of culturing the labeled cell in the absence of the mitochondrial indicator.

Moreover, the mitochondrial indicator used in this embodiment of the present invention may be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment of the present invention, M7512, T3168, T668 or R302 are preferable as a mitochondrial indicator.

In the fourth embodiment, the present invention provides a method of evaluating ratio of a cardiomyocyte in a cardiomyocyte-containing cell mixture, wherein said method comprises the following steps:
  (1) a step of labeling the cardiomyocyte-containing cell mixture with a mitochondrial indicator; and
  (2) a step of measuring ratio of the cardiomyocyte to a non-cardiomyocyte on the basis of a relative content of cellular mitochondria and/or a relative mitochondrial transmembrane potential of the cell.

In the context of the fourth embodiment, the cardiomyocyte-containing cell mixture may be differentiated cell mixture which is derived from a cell mixture derived from a whole heart or a cell having an ability to differentiate to the cardiomyocyte.

Further, the cell having an ability to differentiate to the cardiomyocyte may be selected from the group consisting of a stem cell, a progenitor cell and an egg cell.

Moreover, the mitochondrial indicator used in this embodiment of the present invention may be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment, M7512, T3168, T668 or R302 are preferable as a mitochondrial indicator.

DETAILED DESCRIPTION OF THE INVENTION

As set forth above, in one embodiment, the present invention provides a method of selecting a cardiomyocyte from a cardiomyocyte-containing cell mixture without genetic alteration of the cardiomyocyte, on the basis of a relative content of cellular mitochondria and/or a relative mitochondrial transmembrane potential of the cell.

It is possible to measure a relative content of cellular mitochondria and/or a relative mitochondrial transmembrane potential of the cell by labeling a cardiomyocyte-containing cell mixture with a mitochondrial indicator.

The term "cardiomyocyte-containing cell mixture" as used herein represents any types of a cell mixture consisting of a cardiomyocyte and other types of cells. For example, the "cardiomyocyte-containing cell mixture" includes, but is not limited to, a cell mixture derived from a whole heart or a cell mixture derived from a cell having an ability to differentiate to the cardiomyocyte. The term "a cell mixture derived from a whole heart" as used herein represents a cell mixture consisting of a cardiomyocyte, an endothelial cell, a stromal cell, a smooth muscle cell and so on, which is obtainable by enzymatic treatment of homogeneic or heterogeneic cardiac tissue (heart) using various enzymes. Further, the term "cell mixture derived from a cell having an ability to differentiate to the cardiomyocyte" as used herein represents a cell mixture consisting of a cardiomyocyte, a non-cardiomyocyte, an undifferentiated cell, a neuronal cell, and an epithelial cell which is obtainable by culturing a cell having an ability to differentiate to the cardiomyocyte (for example, a stem cell such as an embryonic stem cell and a somatic stem cell, a progenitor cell, and an egg cell such as a fertilized egg cell and a somatic cell clone) under the condition of inducing cell differentiation from the cell having an ability to differentiate to the cardiomyocyte to the cardiomyocyte.

The content of cellular mitochondria and mitochondrial transmembrane potential can be quantified by labeling an intracellular mitochondria with a mitochondrial indicator. However, the absolute value of mitochondrial indicator-derived signal which reflects the content of mitochondria and mitochondrial transmembrane potential varies depending on the maturity of the cardiomyocyte to be analyzed and exposure condition to labeling agents such as kinds of the labeling agents and exposure time to the labeling agents. Therefore, the important feature of the present invention is not the absolute value of mitochondrial indicator-derived signal, but the relationship between an amount of the mitochondrial indicator-derived signal of the cardiomyocyte and that of a non-cardiomyocyte. In the present invention, it is possible to select a cell exhibiting relatively higher fluorescence intensity as a cardiomyocyte. First, based on a preliminary experiment using a specimen of a cardiomyocyte-containing cell mixture which would actually be used in the present invention, the definition of the desired cardiomyocyte population (i.e., the relation between the content of mitochondria and/or the extent of the mitochondrial transmembrane potential and the cardiomyocyte) is properly determined in accordance with the purpose of the invention. Specifically, in the preliminary experiment, based on the values of the content of mitochondria and/or the extent of the mitochondrial transmembrane potential used as indicators, an amount of the mitochondrial indicator-derived signal of a cell to be selected is classified into several groups. A cell exhibiting relatively higher content of intracellular mitochondria and a cell exhibiting relatively higher mitochondrial transmembrane potential should be collected based on the values of the content of mitochondria and/or the extent of the mitochondrial transmembrane potential used as indicators.

In the present invention, the term "mitochondrial indicator" represents, but is not limited to, a material such as a material which can specifically label mitochondria in the living cell and can demonstrate the content of mitochondria, a material which can specifically label mitochondria in the living cell and can demonstrate the mitochondrial transmembrane potential, or a material which can specifically label mitochondria in the living cell and can demonstrate both the content of mitochondria and the mitochondrial transmembrane potential. For example, the "mitochondrial indicator" includes, but is not limited to, (1) a material having a property to generate fluorescent emission and having an ability to bind the mitochondrial structural material (e.g., a protein, a lipid, a sugar chain, a nucleic acid, or a metabolite thereof, and so on); (2) a material having a property to generate fluorescent emission and to be incorporated into mitochondria by the action of mitochondrial transmembrane potential; (3) a material which is converted to form a material having a property to generate fluorescent emission by the action of mitochondrial structural material; or (4) a material which loses an ability to diffuse outside the mitochondria by the action of mitochondria structural material.

In the present invention, it is possible to use a mitochondrial indicator such as, but not being limited to, A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, S7563, T639, T668, T669 or T3168 (the product numbers of compounds: all available from Molecular Probes) as an exemplary mitochondrial indicator; more preferably, M7514, M7510, M7511, M7512, M7513, M22425, M22426, T668, R302, or T3168; most preferably, T668, R302, M7514 or T3168. The chemical structures of the mitochondrial indicators described above used in the present invention are listed as follows:

[Chem 1]

| [Chem 1] Structure for A1372 | |
|---|---|
| Molecular Formula: | C$_{26}$H$_{38}$BrN$_3$ |
| Molecular Weight: | 472.51 |
| CAS Number: | 75168-11-5 |
| Name: | Acridinium, 3,6-bis(dimethylamino)-10-nonyl-, bromide |

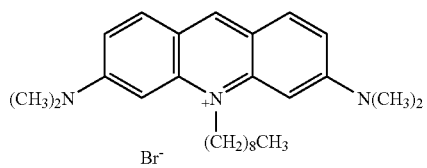

| [Chem 2] Structure for D273 | |
|---|---|
| Molecular Formula: | C$_{29}$H$_{37}$IN$_2$O$_2$ |
| Molecular Weight: | 572.53 |
| CAS Number: | 53213-82-4 |
| Name: | Benzoxazolium, 3-hexyl-2-(3-(3-hexyl-2(3H)-benzoxazolylidene)-1-propenyl)-, iodide |

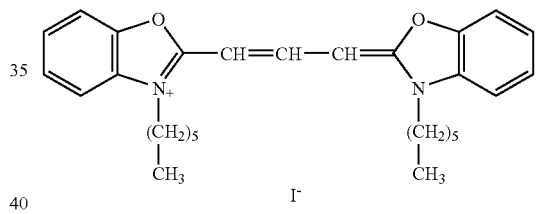

| [Chem 3] Structure for D288 | |
|---|---|
| Molecular Formula: | C$_{16}$H$_{19}$IN$_2$ |
| Molecular Weight: | 366.24 |
| CAS Number: | 959-81-9 |
| Name: | Pyridinium, 4-(2-(4-(dimethylamino)phenyl)ethenyl)-1-methyl, iodide |

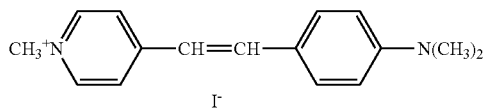

| [Chem 4] Structure for D308 | |
|---|---|
| Molecular Formula: | C$_{16}$H$_{19}$IN$_2$ |
| Molecular Weight: | 366.24 |
| CAS Number: | 2156-29-8 |
| Name: | Pyridinium, 2-(2-(4-(dimethylamino)phenyl)ethenyl)-1-methyl, iodide |

[Chem 4]
Structure for D308

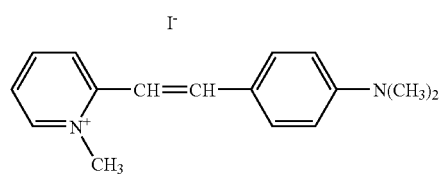

[Chem 5]
Structure for D378

| | |
|---|---|
| Molecular Formula: | $C_{31}H_{41}N_2O_2I$ |
| Molecular Weight: | 600.58 |
| CAS Number: | N/A |
| Name: | N/A |

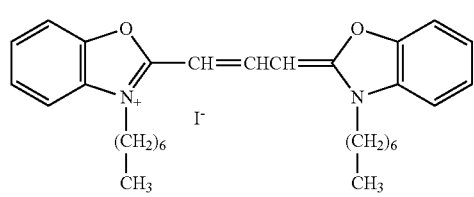

[Chem 6]
Structure for D426

| | |
|---|---|
| Molecular Formula: | $C_{17}H_{21}IN_2$ |
| Molecular Weight: | 380.27 |
| CAS Number: | 3785-01-1 |
| Name: | pyridinium, 2-(2-(4-dimethylamino)phenyl)ethenyl)-1-ethyl, iodide |

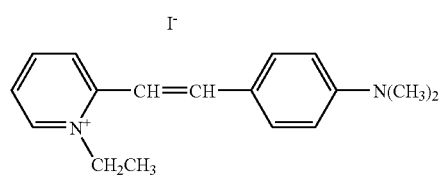

[Chem 7]
Structure for D632

| | |
|---|---|
| Molecular Formula: | $C_{21}H_{18}N_2O_3$ |
| Molecular Weight: | 346.38 |
| CAS Number: | 109244-58-8 |
| Name: | Benzoic acid, 2-(3,6-diamino-9H-xanthene-9-yl)-, methyl ester |

[Chem 7]
Structure for D632

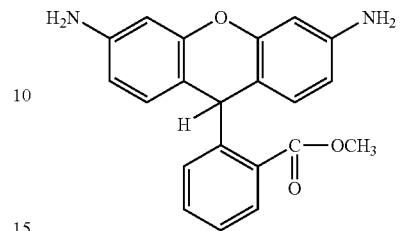

[Chem 8]
Structure for D633

| | |
|---|---|
| Molecular Formula: | $C_{28}H_{32}N_2O_3$ |
| Molecular Weight: | 444.57 |
| CAS Number: | N/A |
| Name: | N/A |

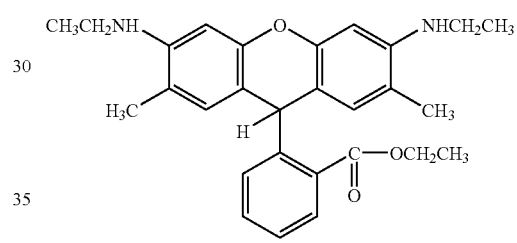

[Chem 9]
Structure for D22421

| | |
|---|---|
| Molecular Formula: | $C_{27}H_{21}IN_2O_2$ |
| Molecular Weight: | 532.38 |
| CAS Number: | N/A |
| Name: | N/A |

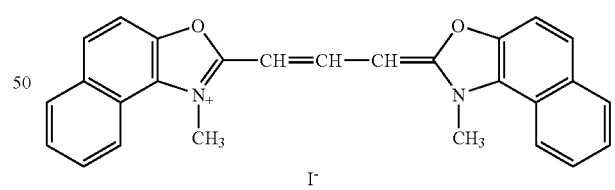

[Chem 10]
Structure for D23806

| | |
|---|---|
| INGREDIENT A: | dihydrorhodamine 123 |
| Molecular Formula: | $C_{21}H_{18}N_2O_3$ |
| Molecular Weight: | 346.38 |
| CAS Number: | 109244-58-8 |
| Name: | Benzoic acid, 2-(3,6-diamino-9H-xanthene-9-yl)-, methyl ester |

-continued

[Chem 10]
Structure for D23806

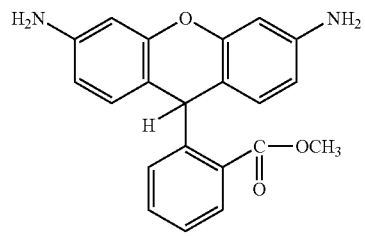 [SMILES: COC(=O)c1ccccc1C1c2ccc(N)cc2Oc2cc(N)ccc21]

[Chem 11]
Structure for L6868

| Molecular Formula: | $C_{28}H_{22}N_4O_6$ |
| Molecular Weight: | 510.50 |
| CAS Number: | 22103-92-0 |
| Name: | 9,9'-Biacridinium, 10,10'-dimethyl- |

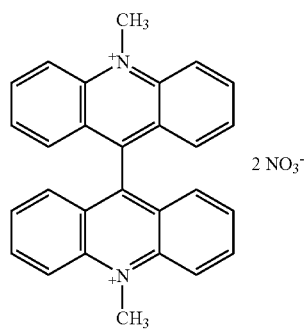

[Chem 12]
Structure for M7502

| Molecular Formula: | $C_{34}H_{30}Cl_3N_3O$ |
| Molecular Weight: | 602.99 |
| CAS Number: | N/A |
| Name: | N/A |

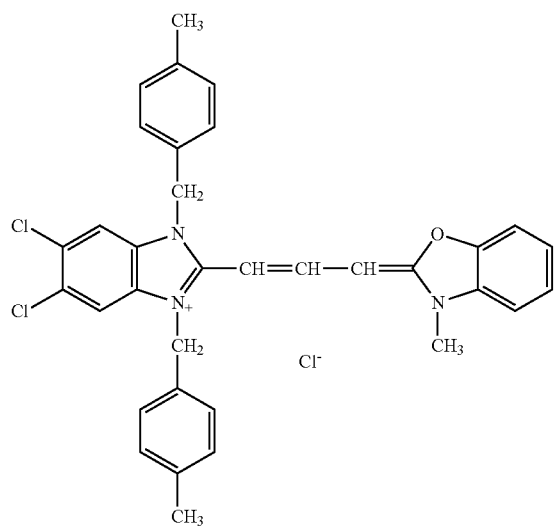 [SMILES: Cc1ccc(Cn2c(C=CC=C3Oc4ccccc4N3C)[n+](Cc3ccc(C)cc3)c3cc(Cl)c(Cl)cc32)cc1 ; [Cl-]]

[Chem 13]
Structure for M7510

| Molecular Formula: | $C_{24}H_{24}Cl_2N_2O$ |
| Molecular Weight: | 427.37 |
| CAS Number: | N/A |
| Name: | N/A |

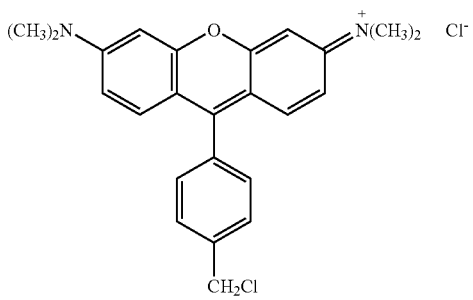

[Chem 14]
Structure for M7511

| Molecular Formula: | $C_{24}H_{25}ClN_2O$ |
| Molecular Weight: | 392.93 |
| CAS Number: | N/A |
| Name: | N/A |

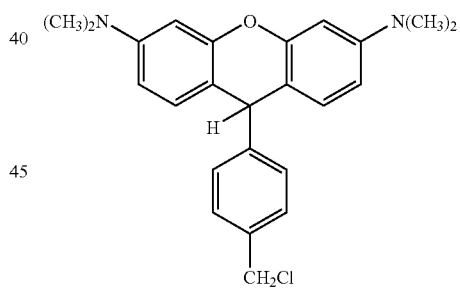

[Chem 15]
Structure for M7512

| Molecular Formula: | $C_{32}H_{32}Cl_2N_2O$ |
| Molecular Weight: | 531.52 |
| CAS Number: | 167095-09-2 |
| Name: | 1H,5H,11H,15H-Xantheno[2,3,4-ij:5,6,7-i'j']diquinolizin-18-ium, 9-[4-(chloromethyl)phenyl]-2,3,6,7,12,13,16,17-octahydro-, chloride |

[Chem 15]
Structure for M7512

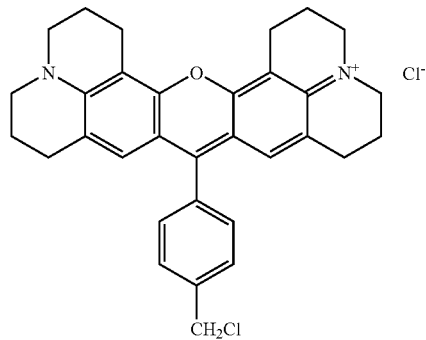

[Chem 16]
Structure for M7513

| | |
|---|---|
| Molecular Formula: | $C_{32}H_{33}ClN_2O$ |
| Molecular Weight: | 497.08 |
| CAS Number: | 167095-08-1 |
| Name: | 1H,5H,9H,11H,15H-Xantheno(2,3,4-ij:5,6,7-i'j')diquinolizine, 9-[4-(chloromethyl)phenyl]-2,3,6,7,12,13,16,17-octahydro- |

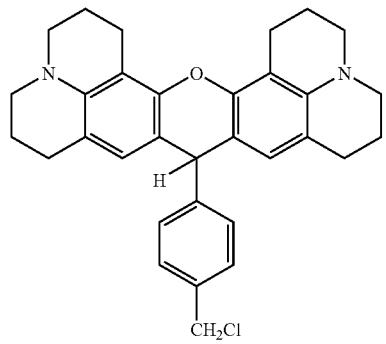

[Chem 17]
Structure for M7514

| | |
|---|---|
| Molecular Formula: | $C_{34}H_{28}Cl_5N_3O$ |
| Molecular Weight: | 671.88 |
| CAS Number: | 201860-17-5 |
| Name: | Benzoxazolium, 2-[3-[5,6-dichloro-1,3-bis[[4-(chloromethyl)phenyl]methyl]-1,3-dihydro-2H-benzimidazol-2-ylidene]-1-propenyl]-3-methyl-, chloride |

[Chem 17]
Structure for M7514

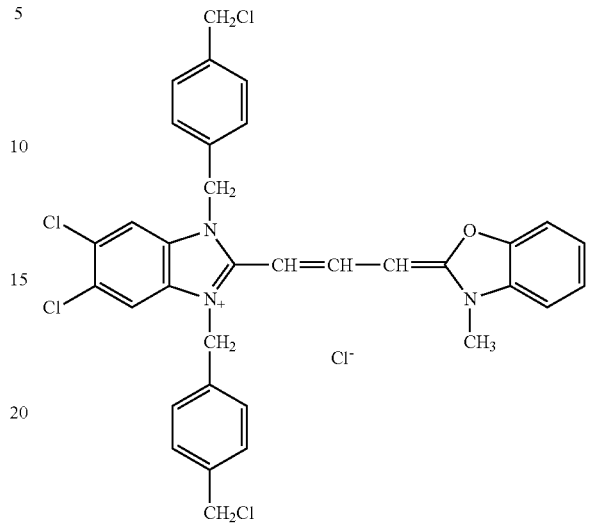

[Chem 18]
Structure for M22422

| | |
|---|---|
| Molecular Formula: | $C_{35}H_{33}ClF_6N_2O$ |
| Molecular Weight: | 647.10 |
| CAS Number: | N/A |
| Name: | N/A |

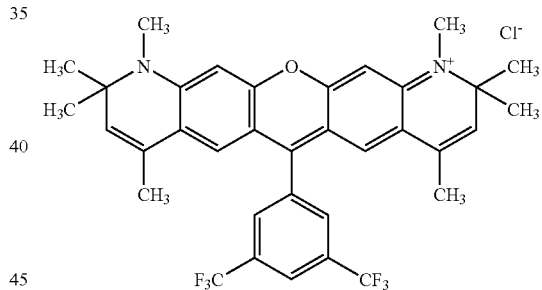

[Chem 19]
Structure for M22423

| | |
|---|---|
| Molecular Formula: | $C_{26}H_{26}ClN_3O_5$ |
| Molecular Weight: | 495.96 |
| CAS Number: | 137993-41-0 |
| Name: | 1H,5H,11H,15H-Xantheno(2,3,4-ij:5,6,7-i'j')diquinolizin-18-ium, 9-cyano-2,3,6,7,12,13,16,17-octahydro-, perchlorate |

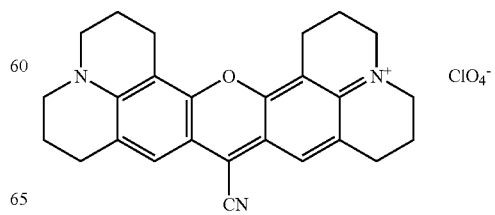

[Chem 20]
Structure for M22425

| | |
|---|---|
| Molecular Formula: | C$_{39}$H$_{36}$Cl$_5$N$_3$ |
| Molecular Weight: | 724.00 |
| CAS Number: | N/A |
| Name: | N/A |

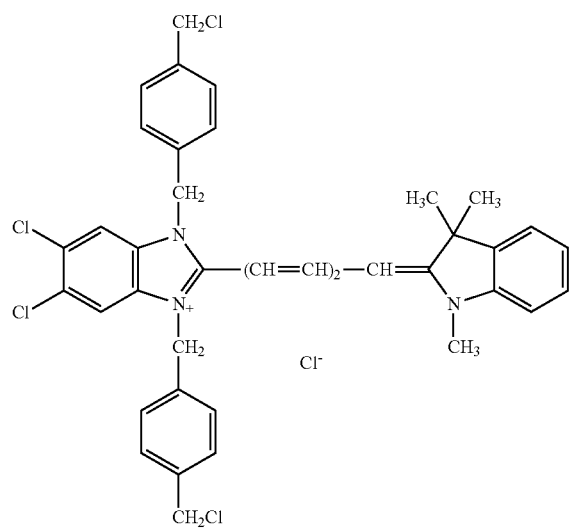

[Chem 21]
Structure for M22426

| | |
|---|---|
| Molecular Formula: | C$_{34}$H$_{36}$Cl$_2$N$_2$ |
| Molecular Weight: | 543.58 |
| CAS Number: | N/A |
| Name: | N/A |

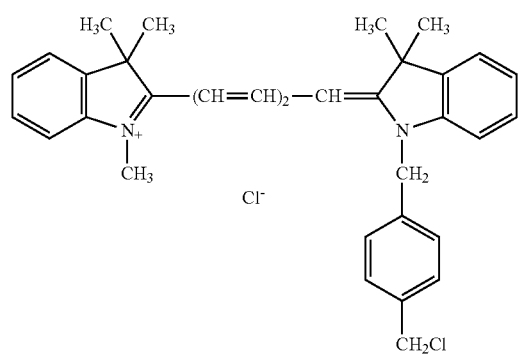

[Chem 22]
Structure for R302

| | |
|---|---|
| Molecular Formula: | C$_{21}$H$_{17}$ClN$_2$O$_3$ |
| Molecular Weight: | 380.83 |
| CAS Number: | 62669-70-9 |
| Name: | Xanthylium, 3,6-diamino-9-(2-(methoxycarbonyl)phenyl, chloride |

-continued

[Chem 22]
Structure for R302

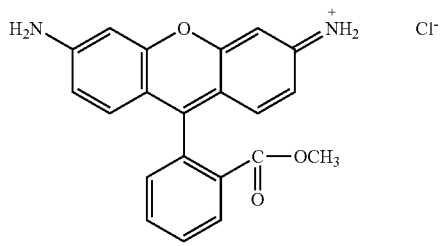

[Chem 23]
Structure for R634

| | |
|---|---|
| Molecular Formula: | C$_{28}$H$_{31}$ClN$_2$O$_3$ |
| Molecular Weight: | 479.02 |
| CAS Number: | 989-38-8 |
| Name: | Xanthylium, 9-(2-(ethoxycarbonyl)phenyl)-3,6-bis(ethylamino)-2,7-dimethyl, chloride |

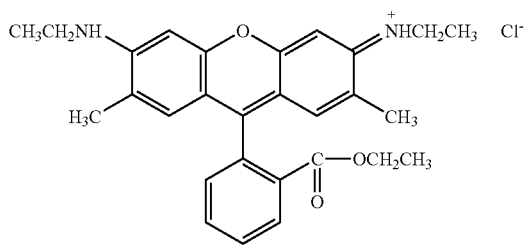

[Chem 24]
Structure for R648

| | |
|---|---|
| Molecular Formula: | C$_{34}$H$_{43}$ClN$_2$O$_7$ |
| Molecular Weight: | 627.18 |
| CAS Number: | N/A |
| Name: | N/A |

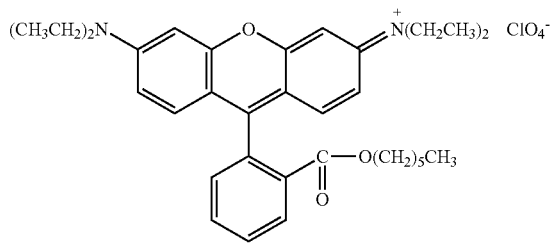

[Chem 25]
Structure for R14060

| | |
|---|---|
| Molecular Formula: | C$_{23}$H$_{19}$F$_5$N$_2$O |
| Molecular Weight: | 434.41 |
| CAS Number: | N/A |
| Name: | N/A |

[Chem 25]
Structure for R14060

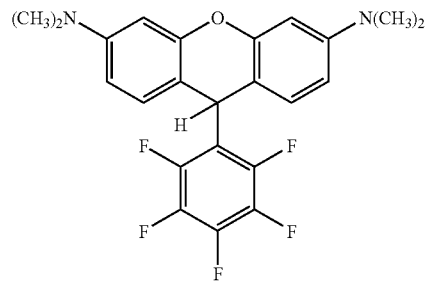

[Chem 26]
Structure for R22420

| | |
|---|---|
| Molecular Formula: | $C_{21}H_{17}ClN_2O_3$ |
| Molecular Weight: | 380.83 |
| CAS Number: | 62669-70-9 |
| Name: | Xanthylium, 3,6-diamino-9-(2-(methoxycarbonyl)phenyl, chloride |

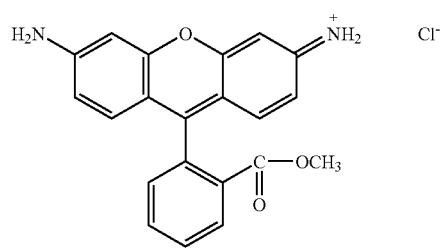

[Chem 27]
Structure for T639

| | |
|---|---|
| Molecular Formula: | $C_{23}H_{23}N_2OCl$ |
| Molecular Weight: | 378.90 |
| CAS Number: | 6837-70-3 |
| Name: | Xanthylium, 3,6-bis(dimethylamino)-9-phenyl, chloride |

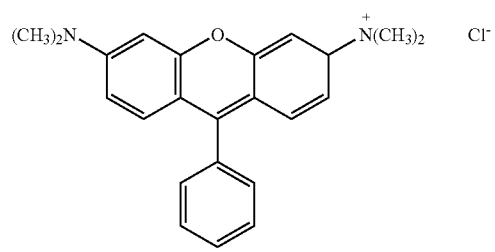

[Chem 28]
Structure for T668

| | |
|---|---|
| Molecular Formula: | $C_{25}H_{25}ClN_2O_7$ |
| Molecular Weight: | 500.93 |
| CAS Number: | 115532-50-8 |
| Name: | Xanthylium, 3,6-bis(dimethylamino)-9-(2-(methoxycarbonyl)phenyl)-, perchlorate |

[Chem 28]
Structure for T668

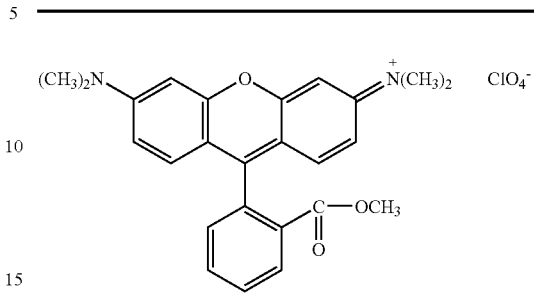

[Chem 29]
Structure for T669

| | |
|---|---|
| Molecular Formula: | $C_{26}H_{27}ClN_2O_7$ |
| Molecular Weight: | 514.96 |
| CAS Number: | 115532-52-0 |
| Name: | Xanthylium, 3,6-bis(dimethylamino)-9-[2-(ethoxycarbonyl)phenyl]-, perchlorate |

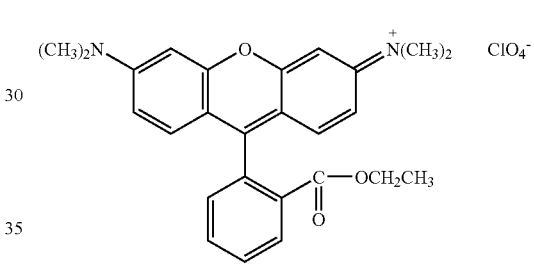

[Chem 30]
Structure for T3168

| | |
|---|---|
| Molecular Formula: | $C_{25}H_{27}Cl_4IN_4$ |
| Molecular Weight: | 652.23 |
| CAS Number: | 47729-63-5 |
| Name: | 1H-Benzimidazolium, 5,6-dichloro-2-[3-(5,6-dichloro-1,3-diethyl-1,3-dihydro-2H-benzimidazol-2-ylidene)-1-propenyl]-1,3-diethyl-, iodide, (E)- |

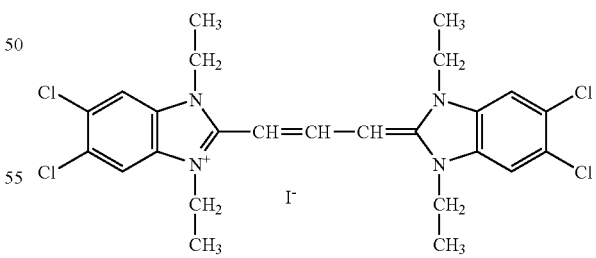

In addition, S7563, S7567 and S7585 (the product numbers of the compounds: all available from Molecular Probes) can also be used as a mitochondrial indicator.

It is known in the art that each mitochondrial indicator has a specific excitation wavelength and generates fluorescence emission of a specific wavelength. For example, M7514 generates fluorescence emission of 516 nm emitted by excitation wavelength of 490 nm, and T3168 generates fluorescence emission of 590 nm emitted by excitation wavelength of 535 nm.

As described above, a cardiomyocyte exhibits more intensive fluorescence intensity than other types of cells when a cardiomyocyte-containing cell mixture is labeled with a mitochondrial indicator, since the cardiomyocyte contains relatively higher content of intracellular mitochondria and has relatively higher mitochondrial transmembrane potential than other types of cells. First of all, in the present invention, the content of the intracellular mitochondria and/or the mitochondrial transmembrane potential are measured for each cell contained in the labeled cardiomyocyte-containing cell mixture. Next, a cell exhibiting more intensive fluorescence intensity is defined as a cardiomyocyte. On the basis of the content of mitochondria and/or the mitochondrial transmembrane potential as measured, a cardiomyocyte is isolated as the following: a cell population containing relatively high content of mitochondria; a cell population containing mitochondria with relatively high transmembrane potential; or a cell population consisting of a cell containing relatively high content of mitochondria and relatively high transmembrane potential.

For example, when a cardiomyocyte-containing cell mixture is labeled with the above described fluorescence luminescent mitochondrial indicators, a cardiomyocyte (which exhibits relatively intensive fluorescence intensity due to relatively high content of mitochondria and mitochondria demonstrating relatively high transmembrane potential) can be discriminated from other types of cells than the cardiomyocyte (i.e., the cells which exhibit relatively less-intensive fluorescence intensity based on the labels with the mitochondrial indicators due to relatively low content of mitochondria or mitochondria demonstrating relatively low transmembrane potential) using a cell sorter. As a result of cell sorting, a viable cardiomyocyte can be selected without genetic alteration of a cardiomyocyte. Cell sorter used in the present invention may not be limited to a specific device as long as viable fluorescent labeled cells can be sorted. For example, Fluorescent Activated Cell Sorter (FACS (registered trademark); BD, Franklin Lakes, N.J. USA) and other cell sorting devices (available from Beckman, Coulter, Cytomation, and so on) can be used as a specific cell sorting device in the present invention.

A cardiomyocyte may be selected immediately after labeling a cardiomyocyte-containing cell mixture with a mitochondrial indicator. However, if it is desirable to select a cardiomyocyte from a cardiomyocyte-containing cell mixture more unfailingly, the cardiomyocyte may be selected after the cell is labeled with a mitochondrial indicator followed by culturing of the labeled cell in the absence of the mitochondrial indicator. During culturing of the labeled cell in the absence of the mitochondrial indicator after it is labeled with the mitochondrial indicator, the content of the mitochondrial indicator existing in a single cell decreases as the cell undergoes a cell division. Therefore, as the culturing period of the proliferative cell becomes longer, the content of the intracellular mitochondrial indicator decreases and the fluorescence intensity also decreases. On the other hand, since a cardiomyocyte is defined as a cell losing a mitotic capacity or a cell with a significantly decreased level of a mitotic capacity, even after a longer period of culture, the content of the mitochondrial indicator existing in a single cell decreases less than other types of cells and, thus, can maintain relatively higher fluorescence intensity. Therefore, it is possible to select a cardiomyocyte more unfailingly, due to the difference in the labeling intensity between the cardiomyocyte and a non-cardiomyocyte after labeling a cardiomyocyte-containing cell mixture with a mitochondrial indicator followed by further culturing the cells in the absence of the mitochondrial indicator for a certain period, more specifically for a few days.

Further, in the second embodiment, the present invention provides a method of enriching a cardiomyocyte from a cardiomyocyte-containing cell mixture without genetic alteration of the cardiomyocyte, wherein said method comprises the following steps:
(1) a step of labeling the cardiomyocyte-containing cell mixture with a mitochondrial indicator; and
(2) a step of selecting the cardiomyocyte on the basis of a relative content of cellular mitochondria and/or a relative mitochondrial transmembrane potential of the cell.

In the context of this embodiment, the cardiomyocyte-containing cell mixture may be a cell mixture derived from a whole heart or a cell mixture derived from a cell having an ability to differentiate to a cardiomyocyte. Since the term "a cell mixture derived from a whole heart" as used herein represents a mixture of a cardiomyocyte and a non-cardiomyocyte, the "cell mixture derived from a whole heart" may cause a clinical risk of a serious side effect against the recipient's cardiac tissue (heart) due to the existence of a non-cardiomyocyte when the mixture is used for cardiac transplantation without any pre-treatment. Therefore, for transplanting a cardiomyocyte to a recipient more safely and surely, it is preferable to enhance the percentage of the cardiomyocyte in the cardiomyocyte-containing cell mixture, i.e., to enrich the cardiomyocyte as much as possible before transplantation. Further, for example, a cell having an ability to differentiate to a cardiomyocyte may be selected from the group consisting of a stem cell, a progenitor cell, and an egg cell.

To enrich the cardiomyocyte unfailingly in this method, after the step (1) and before the step (2), the method of the present invention may further comprise a step of culturing the labeled cell in the absence of the mitochondrial indicator. This step ensures the enhanced level of a relative intracellular fluorescence intensity of the cardiomyocyte in relation to the reduced level of fluorescence intensity of other types of the cells and enables enrichment of the cardiomyocyte more unfailingly.

As described above, the mitochondrial indicator used in this embodiment of the present invention may be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment of the present invention, M7512, T3168, T668 or R302 are preferable as a mitochondrial indicator.

Further, in the third embodiment of the present invention, the present invention provides a method of producing a cardiomyocyte from a cardiomyocyte-containing cell mixture without genetic alteration of the cardiomyocyte, wherein said method comprises the following steps:
(1) a step of differentiating and inducing the cardiomyocyte from a cell having an ability to differentiate to the cardiomyocyte to prepare a cardiomyocyte-containing cell mixture;
(2) a step of labeling cardiomyocyte-containing cell mixture with a mitochondrial indicator; and
(3) a step of selecting a cardiomyocyte on the basis of a relative content of cellular mitochondria and/or a relative mitochondrial transmembrane potential of the cell.

In the context of this embodiment, cardiomyocyte-containing cell mixture may be a cell mixture derived from a whole heart or cell mixture derived from a cell having an ability to differentiate to the cardiomyocyte. Since the term "a cell mixture derived from a whole heart" as used herein represents a mixture of a cardiomyocyte and a non-cardiomyocyte, the "cell mixture derived from a whole heart" may cause a clinical risk of a serious side effect against the recipient cardiac tissue (heart) due to the existence of a non-cardiomyocyte when the mixture is used for cardiac transplantation without any pre-treatment. Therefore, for transplanting the cardiomyocyte to a recipient more safely and surely, it is preferable to enhance the percentage of the cardiomyocyte in the cardiomyocyte-containing cell mixture, i.e., to enrich the cardiomyocyte as much as possible before transplantation. Further, for example, a cell having an ability to differentiate to the cardiomyocyte may be selected from the group consisting of a stem cell, a progenitor cell, and an egg cell.

To produce the cardiomyocyte unfailingly in this method, after the step (1) and before the step (2), the method of the present invention may further comprise a step of culturing the labeled cell in the absence of the mitochondrial indicator.

As described above, the mitochondrial indicator used in this embodiment may also be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment, M7512, T3168, T668 or R302 are preferable as a mitochondrial indicator.

It has been already developed in the art as a method of differentiating and inducing a cardiomyocyte that a cardiomyocyte can be differentiated and induced from a pluripotent stem cell which is less differentiated and has a variety of differentiation potential. The term "a pluripotent stem cell" is defined as a cell having an ability to indefinitely proliferate or for prolonged periods under the in vitro culture conditions keeping the cell with an undifferentiated state, having a normal karyotype (chromosome 1 type), and having an ability to differentiate any cell lineages derived from any of the triderm (ectoderm, mesoderm, and endoderm) under appropriate conditions. Currently, three types of cells are well known in the art as a pluripotent stem cell, i.e., an embryonic stem cell (ES cell) which is isolated from an early embryo, an embryonic germ cell (EG cell) which is isolated from a primordial germ cell at fetal stage, and an adult-type pluripotent stem cell (also referred to as a multipotent adult progenitor cell (MAPC)) which is isolated from adult bone marrow.

For example, a method of differentiating and inducing a cardiomyocyte from an embryonic stem cell (as an example of a pluripotent stem cell) may be selected from the group consisting of Floating culture of embryoid body-like aggregates, Hanging-drop culture, Co-culture with feeder cells, Rotation culture, Soft agar culture, and Microcarrier culture.

For example, in the case of Floating culture of embryoid body-like aggregates, it was known that an autonomously pulsating cardiomyocyte can be prepared by differentiation and induction of an ES cell, wherein the method comprises the following steps: a step of suspending an embryonic stem cell in the culture medium at the concentration of several hundreds of cells/mL in which each ES cell is in single cell state (i.e., the state in which each cells are dispersed in the aquaous phase without intercellular adhesion by an enzymatic treatment),.a step of culturing the cells under the suspension culture in the absence of a differentiation inhibitory factor (such as leukemia inhibitory factor: LIF), a step of forming an early embyro-like structure known as an embryoid body (EB) which is formed by adhering and aggregating ES cells to each other, and a step of culturing EB under the condition of suspension culture or of adhesion culture.

In the case of Hanging-drop culture, it is known that an autonomously pulsating cardiomyocyte can be prepared by differentiation and induction of an ES cell, wherein the method comprises the following steps: a step of preparing a droplet consisting of 20 μl of culture medium including several hundreds of cells inside the lid of the culture dish, a step of placing the lid of the culture dish with a droplet to cover the culture dish, a step of forming a cell mass at the bottom (i.e., the tip) of the droplet, and a step of differentiating and inducing an autonomously pulsating cardiomyocyte from the cell mass.

In the case of Co-culture with feeder cells, it is known that an autonomously pulsating cardiomyocyte can be prepared by differentiation and induction of an ES cell, wherein the method comprises the following steps: a step of preparing a feeder layer from a cell having mesenchymal cell-like characteristics, preferably, a cell having marrow stromal cell-like characteristics (such as ST2 cell, OP9 cell, PA6 cell) using a method such as high-density culture, mitomycin C treatment, or radiation irradiation, and a step of culturing an ES cells being in single cell state over the feeder layer.

Further, in the fourth embodiment, the present invention provides a method of evaluating percentage of a cardiomyocyte in a cardiomyocyte-containing cell mixture, wherein said method comprises the following steps:
(1) a step of labeling the cardiomyocyte-containing cell mixture with a mitochondrial indicator; and
(2) a step of measuring the ratio of the cardiomyocyte to a non-cardiomyocyte on the basis of a relative content of cellular mitochondria and/or a step of selecting a cardiomyocyte on the basis of a relative mitochondrial transmembrane potential of the cell.

In the context of this embodiment, the cardiomyocyte-containing cell mixture may be a cell mixture derived from a whole heart or a cell mixture derived from a cell having an ability to differentiate to the cardiomyocyte. Since the term "a cell mixture derived from a whole heart" as used herein represents a mixture of a cardiomyocyte and a non-cardiomyocyte, the "cell mixture derived from a whole heart" may cause a clinical risk of a serious side effect against the recipient's cardiac tissue (heart) due to the existence of a non-cardiomyocyte when the mixture is used for cardiac transplantation without any pre-treatment. Therefore, for transplanting the cardiomyocyte to a recipient more safely and surely, it is preferable to enhance the percentage of the cardiomyocyte in the cardiomyocyte-containing cell mixture, i.e., to enrich the cardiomyocyte, as high as possible before transplantation. Further, for example, a cell having an ability to differentiate to a cardiomyocyte may be selected from the group consisting of a stem cell, a progenitor cell, and an egg cell.

Also in this embodiment, as described above, the mitochondrial indicator used in this embodiment of the present invention may be selected from the group consisting of: A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 and T3168. In this embodiment, M7512, T3168, T668 or R302 are preferable as a mitochondrial indicator.

In the field related to transplantation of a cardiomyocyte, some methods are known for differentiating and inducing a cardiomyocyte and it is expected that a number of methods will be developed in the future as a method of differentiating and inducing a cardiomyocyte. However, as described above, there is a clinical risk caused by a serious side effect against the recipient cardiac tissue (heart) due to the existence of a non-cardiomyocyte when the mixture is used for cardiac transplantation. Thus, it is possible to preliminarily evaluate the reliability of cardiomyocyte preparation to be used in the transplantation by preliminarily evaluating the percentage of a cardiomyocyte in the cardiomyocyte preparation to be transplanted into a cardiac tissue according to this method.

Some methods are known in the art as a method of purifying a cardiomyocyte, such as a method based on antigen-antibody reaction, such as flow cytometry technique, magnetic beads, panning method, and so on (Monoclonal Antibodies: principles and practice, Third Edition (Acad. Press, 1993); Antibody Engineering: A Practical Approach (IRL Press at Oxford University Press, 1996); a method of collecting a cell exhibiting a phenotype of a cardiomyocyte by preliminary incorporating artificial modifications into a gene of a pluripotent stem cell as a parent cell (such as an ES cell) to confer drug resistance or an expression ability of ectopic protein; and cell fractionation method by density gradient centrifugation using a carrier such as sucrose and percoll, which can be easily combined with other methods though the degree of purity is relatively low (Circ Res. 2002 20;91:501-508), and so on.

Effects of the Invention

According to the present invention, it is possible to select a cardiomyocyte from a cardiomyocyte-containing cell mixture without genetic alteration of the cardiomyocyte. Further, according to the present invention, it is also possible to enrich the cardiomyocyte within the cardiomyocyte-containing cell mixture without genetic alteration of the cardiomyocyte and to produce the cardiomyocyte without genetic alteration of the cardiomyocyte. Moreover, it is also possible to evaluate the percentage of the cardiomyocyte in the cardiomyocyte-containing cell mixture prepared by a variety of methods.

According to these embodiments, it is possible to enhance the percentage of the cardiomyocyte in the cardiomyocyte-containing cell mixture and to reduce the various possible side effects against the recipient cardiac tissue (heart) due to the existence of a non-cardiomyocyte upon transplantation.

BRIEF DESCRIPTION OF THE DRAWINGS

FIG. 1 shows a fluorescent image of a cell mixture derived from a whole heart extracted from neonatal rat heart, which was labeled with a mitochondrial indicator, M7512.

FIG. 2 shows a fluorescent image of cell mixture derived from a cell having an ability to differentiate to the cardiomyocyte extracted from mouse embryonic stem cells, which was labeled with a mitochondrial indicator, M7512.

FIG. 3 shows distribution of cell population when a cell mixture derived from a whole heart extract from neonatal rat heart was labeled with a mitochondrial indicator, M7512, in which the amount of fluorescence of each cells was separately detected.

FIG. 4 shows distribution of cell population when a cell mixture derived from a cell having an ability to differentiate to the cardiomyocyte derived from a mouse embryonic stem cell was labeled with a mitochondrial indicator, M7512, in which the amount of fluorescence of each cell was separately detected.

FIG. 5 shows a fluorescent image of a cell mixture derived from a whole heart (shown in FIG. 3), which was stained with an antibody against a cardiomyocyte marker, anti-Sarcomeric α-Actinin Antibody.

FIG. 6 shows a fluorescent image of a cell mixture derived from a cell having an ability to differentiate to a cardiomyocyte (shown in FIG. 4), which was stained with an antibody against a cardiomyocyte marker, anti-Sarcomeric α-Actinin Antibody.

FIG. 7 shows a fluorescent image of a cell population using an antibody against a cardiomyocyte marker, anti-Sarcomeric α-Actinin Antibody, in which the cell population was subjected to distribution analysis and cell sorting by separately detecting the amount of fluorescence of each cell after labeling of a cell mixture derived from a whole heart extracted from neonatal rat heart with a mitochondrial indicator, T3168.

[FIG. 8-1] FIG. 8 shows a result of analysis of a cell population which was subjected to distribution analysis and cell sorting by separately detecting the amount of fluorescence of each cell after labeling of cells extracted from neonatal rat whole heart with a mitochondrial indicator, T668, and a fluorescent image of each cell population using an antibody against a cardiomyocyte marker, anti-Sarcomeric α-Actinin Antibody. FIG. 8-1 shows that the cell population derived from neonatal rat heart is separated into 3 groups of the cell population based on T668 fluorescent intensity.

[FIG. 8-2] FIG. 8-2 shows that almost all cells of the cell population with the highest intensity of T668 fluorescent signal consist of a cardiomyocyte and almost all cells of the cell population with the middle fluorescent intensity consist of a non-cardiomyocyte.

[FIG. 8-3] FIG. 8-3 shows that cells of interest can also be obtained using R302, as well as T668.

[FIG. 9-1] FIG. 9 shows cell population analysis of a rat fetal cell derived from a whole heart with a mitochondrial indicator, T668, and immunostaining of the sorted cells with anti-Actinin antibody. FIG. 9-1 shows that the cell population derived from fetal rat heart of 13th day post conception is separated into 3 groups of the cell population based on T668 fluorescent intensity.

[FIG. 9-2] FIG. 9-2 shows that almost all cells of the cell population with the highest intensity of T668 consist of a cardiomyocyte and almost all cells of the cell population with the middle fluorescent population consist of a non-cardiomyocyte.

[FIG. 10-1] FIG. 10 shows staining of whole fetal cells with a mitochondrial indicator, T668, and purification of a cardiomyocyte. FIG. 10-1 shows that a single cell population derived from fetal rats of 9th day post conception is mainly found by isolating the cells by the fluorescent intensity.

[FIG. 10-2] FIG. 10-2 shows that more than about 95% of T668 labeled cells are found to be a cardiomyocyte by an immunostaining against a cardiomyocyte marker, Actinin.

FIG. 11 shows data of staining and cell population analysis of a rat cell derived from a whole heart from 11th day post conception to 8 days after birth using a mitochondrial indicator, T668.

FIG. 12 shows the data of staining of a population consisting of multiple types of cells derived from a mouse embryonic stem cell with a mitochondrial indicator T668 and an immunostaining of the sorted cell population against Actinin.

Figure 1:
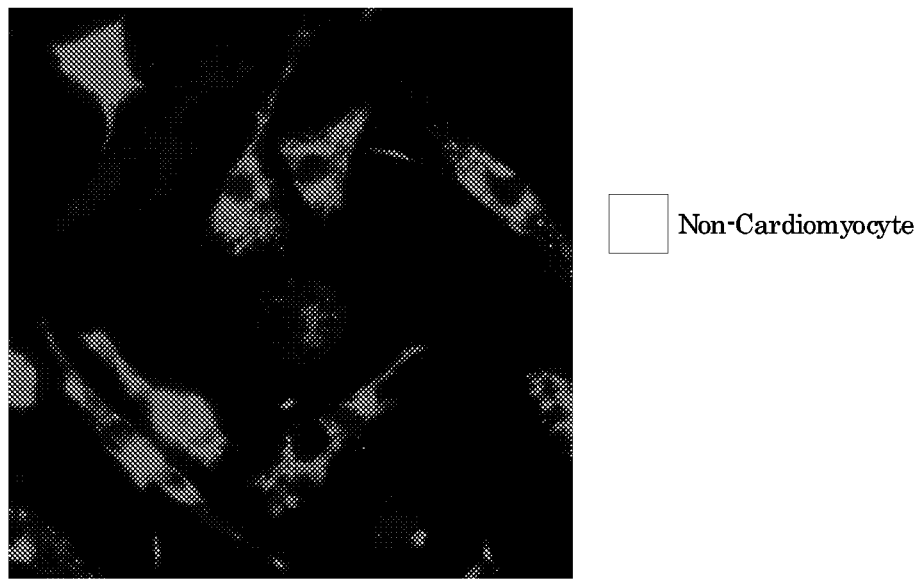
[FIG. 1]

EMBODIMENT OF CONDUCTING THE INVENTION (1) Preparation of a Cardiomyocyte-Containing Cell Mixture:

First, a cardiomyocyte-containing cell mixture is obtained as a cell mixture derived from a whole heart or a cell mixture derived from a stem cell.

The cell mixture derived from a whole heart can be prepared by isolating a cardiac ventricle from an aborted fetus or a neonatal animal, mincing it using forceps, degrading intercellular adhesion using an enzyme such as collagenase to disperse the cells.

The cell mixture derived from a stem cell can be prepared by differentiating and inducing a stem cell such as an embryonic stem cell and a somatic stem cell into a cardiomyocyte using hanging-drop culture method (Bader A, et al., Differentiation, 2001 68: p. 31-43). It is preferable that, when using cell mixture derived from a stem cell, additional treatment for enhancing the degree of differentiation/induction of the cardiomyocyte (such as an addition of all-trans retinoic acid) is conducted on the differentiated/induced cell mixture.

(2) Labeling of a Cell with a Mitochondrial Indicator:

In the present invention, a fluorescence material such as M7512, T3168, T668 or R302 (all available from Molecular Probe) is used as a desirable mitochondrial indicator. Cells are labeled with M7512, T3168, T668 or R302 by incubating of a cell mixture derived from a whole heart or a cell mixture derived from stem cell in the presence of M7512, T3168, T668 or R302 in the culture medium.

By further culturing for several days after labeling the cells with the mitochondrial indicator, it is possible to further amplify the difference between an amount of labeled signal of a cardiomyocyte and that of a non-cardiomyocyte.

(3) Selection of the Cardiomyocyte:

Cell sorter is used to measure the content of mitochondria in the cell mixture derived from a whole heart or the cell mixture derived from a stem cell labeled with M7512, T3168, T668 or R302 and a cell population containing relatively higher amount of mitochondria is isolated as a cardiomyocyte. Fluorescent Activated Cell Sorter (FACS (registered trademark); BD, Franklin Lakes, N.J. USA) is used as a preferable cell sorter for selecting the cardiomyocyte using M7512, T3168, T668 or R302.

(4) Confirmation of the Cardiomyocyte:

A cell exhibiting relatively higher fluorescence intensity is sorted by the above described method and is subject to cell culture. Subsequently, the calculated content and the rate of content of the cardiomyocyte selected by the present method are compared with those selected by a method of discriminating the cardiomyocyte from other types of cells other than the present method, in order to confirm the effectiveness of the present invention. In the present invention, a method of detecting the cardiomyocyte using an antibody against a cardiomyocyte-specific marker (such as myosin heavy chain/light chain, Sarcomeric α-Actinin, troponin I, ANP, GATA-4, Nkx2.5, and MEF-2c) may be used as other method of discriminating the cardiomyocyte from other types of cells. Especially in the present invention, an anti-Sarcomeric α-Actinin Antibody is used to label and select the cardiomyocyte.

EXAMPLES

The following examples are provided to further illustrate the present invention. However, the following examples are in no way to be taken as limiting the technical scope of the invention, but only for exemplification.

Example 1

Labeling of a Cell Mixture Derived from a Whole Heart Extracted from Neonatal Rat Heart with a Mitochondrial Indicator This example was conducted to confirm whether the method of the present invention can be used to detect a cardiomyocyte in a cell mixture derived from a whole heart.

Neonatal rats 1-3 days after birth were sacrificed by cervical dislocation after ether anesthesia, after which the heart of each rats was isolated. Cardiac ventricle isolated from the heart was treated with 0.025% (w/v) of collagenase (available from Warthington Biomedical Corporation) in serum free D-MEM (High-glucose) medium (available from Invitrogen). By digesting the cardiac ventricle using collagenase, cells were dispersed in the medium to prepare a cell mixture derived from a whole heart.

Subsequently, the culture medium was replaced by D-MEM (High-glucose) medium (available from Invitrogen) supplemented with 10% (final concentration) of fetal bovine serum (available from JRH Bioscience). Thus prepared cultured cells were incubated in the culture medium containing 100 nM (final concentration) of a mitochondrial indicator, M7512 (available from Molecular Probe) for 10 minutes at 37° C. After incubation, the cells were washed 4 times using the culture medium and further cultured for 24 hours at 37° C.

Thus labeled cells were observed using a fluorescent microscope. The result is shown in FIG. 1.

FIG. 1 shows that while M7512-based fluorescence is clearly observed in a cardiomyocyte and the cardiomyocyte contains a number of mitochondria within the cell, a non-cardiomyocyte contains only a small number of mitochondria within the cell.

Example 2

Labeling of a Cell Mixture Derived from a Mouse Embryonic Stem Cell with a Mitochondrial Indicator This example was conducted to confirm whether the method of the present invention can be used to detect a cardiomyocyte in cell mixture derived from a stem cell.

Undifferentiated mouse embryonic stem cell was subjected to hanging-drop culture (Bader A, et al., Differentiation, 2001 68: p. 31-43) to differentiate and induce a cardiomyocyte. Specifically, the hanging-drop culture was known whereby the cardiomyocyte can be prepared by differentiation and induction of an ES cell by the present method, wherein the present method comprising the following steps: a step of preparing a droplet consisting of 20 μl of culture medium inside the lid of the culture dish, wherein said droplet includes several hundreds of cells, a step of placing the lid of the culture dish with a droplet to cover the culture dish, a step of forming a cell mass at the bottom of the droplet, i.e., the tip of the droplet, and a step of differentiating and inducing an autonomously pulsating cardiomyocyte from the cell mass. The present invention used α-MEM medium (available from SIGMA) containing 10% (final concentration) of fetal bovine serum (available from EQUITECH-BIO) upon differentiating and inducing the cardiomyocyte.

Fourteen days after differentiation and induction, a cell mass containing an autonomously pulsating cardiomyocyte was confirmed to be formed in the culture vessel, to which $10^{-8}$ M of all trans-retinoic acid was added for further enhancing the degree of differentiation/induction of the cardiomyocyte.

At 21st day from differentiation/induction, a cell mass containing an autonomously pulsating cardiomyocyte was dispersed into separate cells to form a cell mixture. Thus prepared cell mixture was labeled with M7512 under the same condition as that of Example 1 and cultured under the condition of the adhesion culture for further 5 days after removal of M7512. After further culture for 5 days, a cell mass containing an autonomously pulsating cardiomyocyte prepared under the culture condition was observed using a fluorescent microscope. The result is shown in FIG. 2.

Figure 2:
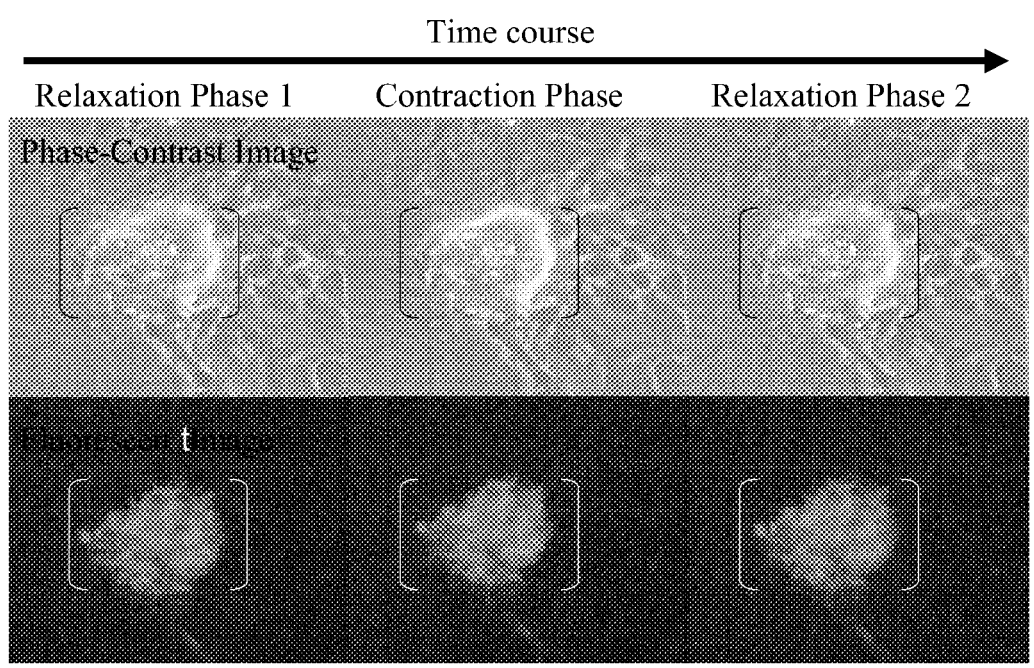
[FIG. 2]

FIG. 2 shows photographs of phase-contrast images (upper panels) and fluorescent images (lower panels) of the cell mass over one pulsating cycle (i.e., a cycle of relaxation phase 1—contraction phase—relaxation phase 2). This result demonstrates that all autonomously pulsating cardiomyocytes were strongly labeled with M7512 as compared with other types of cells. That is to say, M7512 based fluorescence was clearly observed in a cell mass consisting of an autonomously pulsating cardiomyocyte; while M7512 based fluorescence could hardly be observed in a cell around the cell mass.

Example 3

Analysis of Distribution of the Cells of a Cell Mixture Derived from a Whole Heart Labeled with a Mitochondrial Indicator This example was conducted to clarify the amount of a cardiomyocyte contained in a cell mixture derived from a whole heart of Example 1.

The cell mixture derived from a whole heart was prepared in accordance with the method described in Example 1 and labeled with M7512. The labeled cell mixture derived from a whole heart was subjected to analysis of distribution of the cells of the cell mixture derived from a whole heart using FACS (registered trademark) (BD, Franklin Lakes, N.J. USA). The result is shown in FIG. 3.

Figure 3:
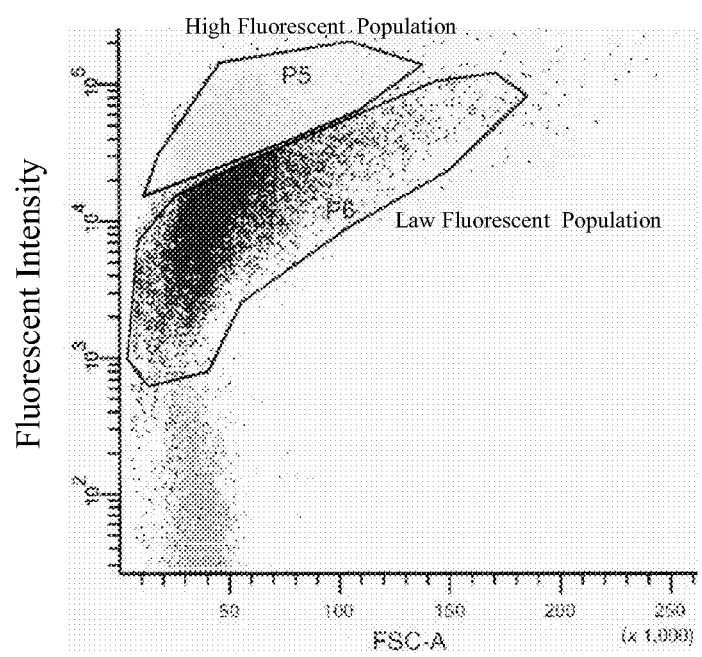
[FIG. 3]

In FIG. 3, "FSC-A" of the horizontal axis demonstrates an indicator of cell size. As depicted in FIG. 3, it is possible to separate the cell mixture derived from a whole heart into two groups of cells, one of which consists of cells with relatively higher fluorescent intensity (depicted as P5 area in FIG. 3) and the other of which consists of cells with relatively lower fluorescent intensity (depicted as P6 area in FIG. 3). In this example, cells of P5 area were sorted as a cardiomyocyte and cells of P6 area were sorted as a non-cardiomyocyte, each then being separately subjected to the cell culture.

Example 4

Analysis of Distribution of the Cells of a Cell Mixture Derived from a Mouse Embryonic Stem Cell Using a Mitochondrial Indicator This example was conducted to clarify the amount of a cardiomyocyte contained in a cell mixture derived from a mouse embryonic stem cell prepared in Example 2.

The cell mixture derived from mouse embryonic stem cell was prepared in accordance with the method described in Example 2 and labeled with M7512. The labeled cell mixture derived from a mouse embryonic stem cell was subjected to analysis of distribution of the cells using FACS (registered trademark) (BD, Franklin Lakes, N.J. USA). The result is shown in FIG. 4.

Figure 4:
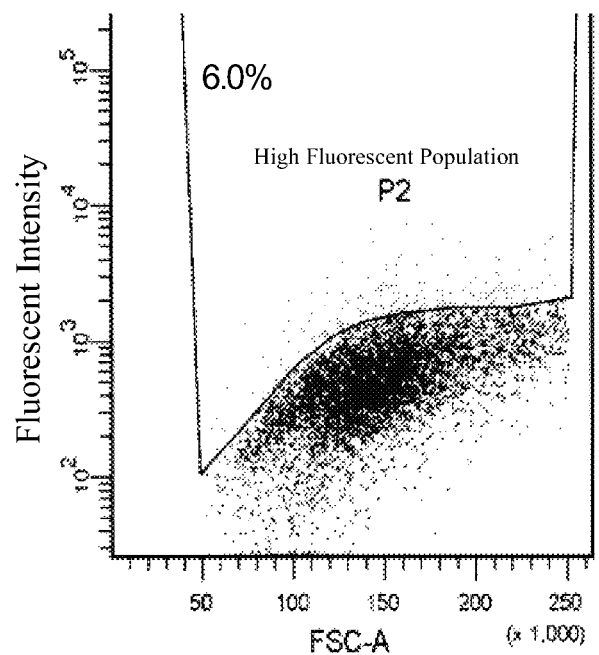
[FIG. 4]

In FIG. 4, "FSC-A" of the horizontal axis demonstrates an indicator of cell size. As depicted in FIG. 4, it is possible to separate the cell mixture derived from a mouse embryonic stem cell into two groups of cells, one of which consist of cells with relatively higher fluorescent intensity (depicted as P2 area in FIG. 4) and the other of which consists of cells with relatively lower fluorescent intensity. In this example, cells of P2 area were sorted as a cardiomyocyte and were subjected to the cell culture.

Example 5

Labeling of Cells Selected from a Cell Mixture Derived from a Whole Heart with a Cardiomyocyte Marker This example was conducted to clarify the degree of enrichment of the cardiomyocyte present in a cell mixture derived from a whole heart by the method of Example 3.

Cell populations of P5 area and P6 area sorted by the method of Example 3 were cultured in α-MEM medium (available from SIGMA) supplemented with 10% (final concentration) of fetal bovine serum (available from EQUITECH-BIO) for 12 hours, which was followed by paraformaldehyde fixation.

Figure 5:
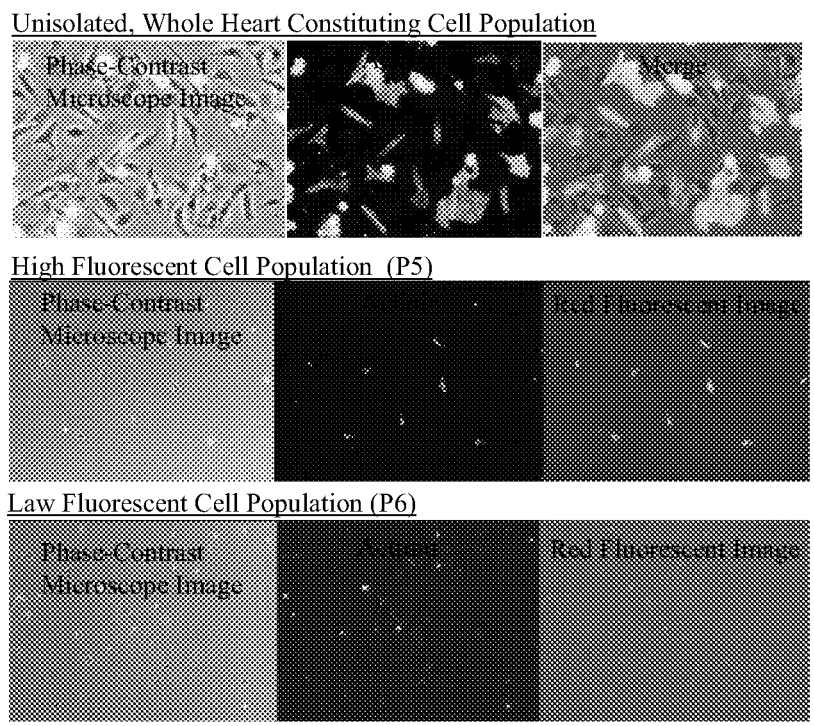
[FIG. 5]

Next, the fixed cells were labeled with a cardiomyocyte marker, mouse anti-Sarcomeric α-Actinin Antibody (available from SIGMA), which were visualized using green fluorescent material-conjugated goat anti-mouse antibody (available from Molecular Probes). The result is shown in FIG. 5. In FIG. 5, the results from the cell mixture derived from a whole heart are shown in the top panels, the results from the cells collected from P5 area in Example 3 are shown in the middle panels, and the results from the cells collected from P6 area in Example 3 are shown in the bottom panels.

The cardiomyocyte recognized by anti-Sarcomeric α-Actinin Antibody and other types of cells were mixed in the cell mixture before selecting the cardiomyocyte by the method of the present invention and the percentage of the cardiomyocyte contained in the total cells was only 30%. On the other hand, more than 99% of cells collected from P5 area were composed of the cardiomyocyte. There was a small amount of the cardiomyocyte remaining in the cells collected from P6 area, the percentage of which was approximately equal to the percentage of the cardiomyocyte before the selection by the present method.

From the result of this example, it is clearly demonstrated that the cardiomyocyte can be selected with high purity and enriched from the cell mixture derived from a whole heart by the method of the present invention.

Example 6

Labeling of Cells Selected from a Cell Mixture Derived from a Mouse Embryonic Stem Cell with a Cardiomyocyte Marker This example was conducted to clarify the degree of enrichment of the cardiomyocyte present in the cell mixture derived from a mouse embryonic stem cell by the method of Example 4.

Cell populations of P2 area and other area sorted by the method of Example 4 were cultured in α-MEM medium (available from SIGMA) supplemented with 10t (final concentration) of fetal bovine serum (available from EQUITECH-BIO) for 12 hours, which was followed by paraformaldehyde fixation.

Figure 6:
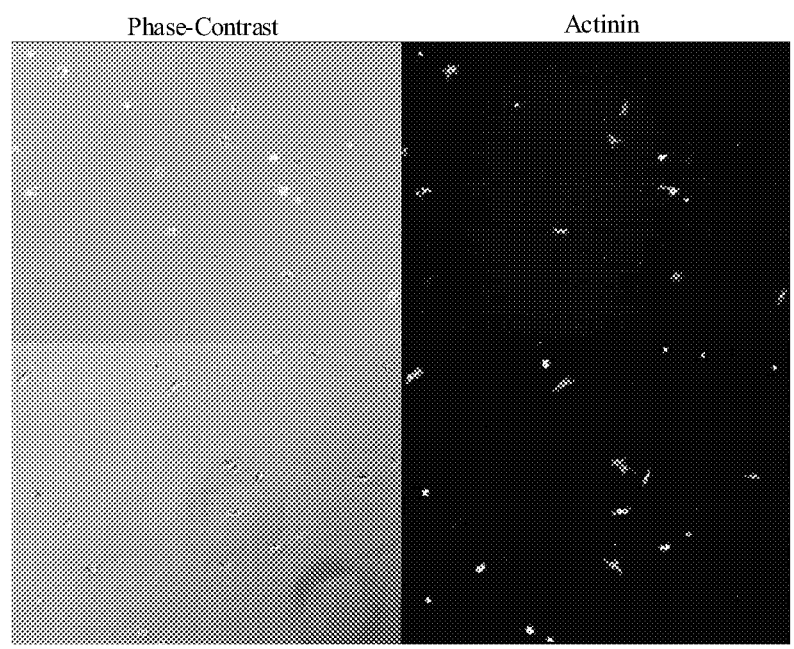
[FIG. 6]

Next, the fixed cells were labeled with a cardiomyocyte marker, mouse anti-Sarcomeric α-Actinin Antibody (available from SIGMA), which were visualized using green fluorescent material-conjugated goat anti-mouse antibody (available from Molecular Probes). The result is shown in FIG. 6. In FIG. 6, the results from the cell mixture derived from a mouse embryonic stem cell are shown in the upper panels and the results from cells collected from P2 area in Example 4 are shown in the lower panels.

The cardiomyocyte recognized by anti-Sarcomeric α-Actinin Antibody and other types of cells were mixed in the cell mixture before Selection of the cardiomyocyte by the method of the present invention and the percentage of the cardiomyocyte contained in the total cells was only 10%. On the other hand, more than 80% of cells collected from P2 area (which exhibit relatively higher fluorescent intensity when labeled with M7512) were demonstrated to be a cardiomyocyte.

From the result shown in this example, it is clearly demonstrated that the cardiomyocyte can also be selected with high purity and enriched from the cell mixture derived from a mouse embryonic stem cell by the method of the present invention.

Example 7

Labeling with a Mitochondrial Indicator, T3168

This example was conducted to confirm whether, when a mitochondrial indicator, T3168, is used to label the cells, it is possible to obtain the similar data to that using M7512.

In this example, the cell mixture derived from a whole heart extracted from a neonatal rat heart, which was labeled with a mitochondrial indicator, was prepared by the same method as that described in Example 1, except that T3168 (available from Molecular Probe) was used as a mitochondrial indicator.

Figure 7:
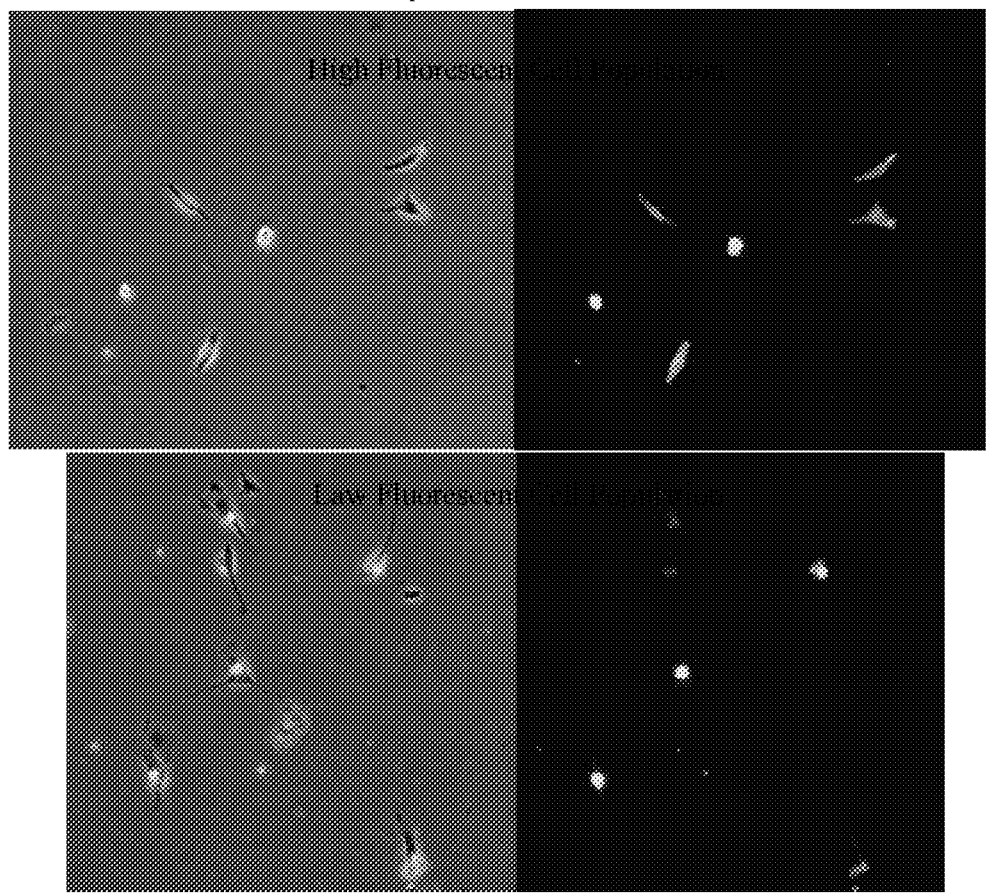
[FIG. 7]

Thus prepared and labeled cell mixture derived from a whole heart was subjected to FACS by the same method as that described in Example 3 to analyze cell distribution and cells with relatively higher fluorescence intensity were selected and collected as a cardiomyocyte. Thus selected cells were cultured followed by paraformaldehyde fixation by the same method as that described in Example 5, which were labeled with mouse anti-Sarcomeric α-Actinin Antibody (available from SIGMA). The result is shown in FIG. 7.

The cardiomyocyte recognized by anti-Sarcomeric α-Actinin Antibody and other types of cells were mixed in the cell mixture before selecting the cardiomyocyte by the method of the present invention and the percentage of the cardiomyocyte contained in the total cells was only 30%. On the other hand, more than 95% of cells exhibiting relatively higher fluorescent intensity were demonstrated to be a cardiomyocyte.

From the result shown in this example, it is clearly demonstrated that the cardiomyocyte can also be selected with high purity and enriched from the cell mixture derived from the cell mixture derived from a whole heart using T3168 as a mitochondrial indicator by the method of the present invention.

Example 8

Figures 1, 8:
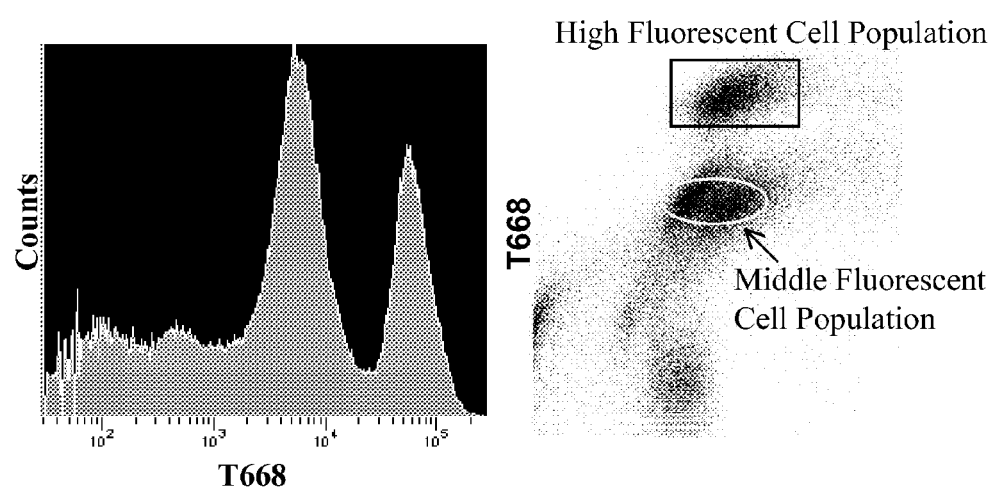
Figures 3, 8:
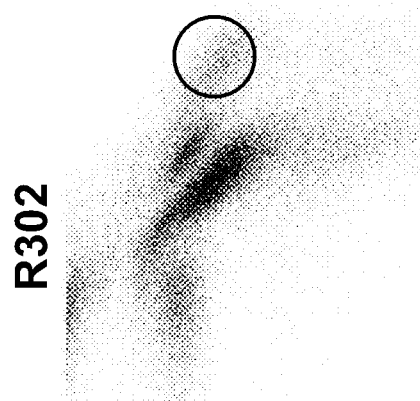

Staining of Neonatal Rat Cells Derived from a Whole Heart by a Mitochondrial Indicator, T668, and Purification of a Cardiomyocyte Neonatal rat heart was treated with 0.025% (w/v) of collagenase (available from SIGMA) and trypsin (available from GIBCO) to collect a cell population. Cells dispersed in the culture medium were exposed to 1 μM (final concentration) of a mitochondrial indicator, T668 (available form Molecular Probe) for 15 minutes at 37° C., washed 3 times, and immediately analyzed by FACS. In consequence, the cells were separated into three groups of cells in accordance with T668-based fluorescent intensity (FIG. 8-1). High fluorescent cell population exhibiting the higher fluorescent intensity and the middle fluorescent cell population were separately sorted.

Then, the cardiomyocyte was identified by immunostaining of the cultured cell using anti-Actinin antibody (FIG. 8-2). In consequence, almost all cells of the cell population with the highest intensity of T668 fluorescent signal consist of a cardiomyocyte and almost all cells of the cell population with the middle fluorescent intensity consist of a non-cardiomyocyte. The same analysis was conducted regarding R302 (available from Molecular Probe) and the similar results were obtained (FIG. 8-3), as well as T668.

Example 9

Staining of Neonatal Rat Cells Derived from a Whole Heart with Mitochondrial Indicators, T668 and M7514, and Comparative Analysis of Transmembrane Potential per Mitochondria Cell population was collected using the same materials and the same method as those described in Example 8. Thus collected cardiomyocytes were stained with a mitochondrial indicator, M7514 (available from Molecular Probe), independent of the transmembrane potential which can specifically stain mitochondria and with a mitochondrial indicator T668 dependent on the transmembrane potential which can also specifically stain mitochondria. The cells were analyzed using FACS immediately after the staining. It is possible to separately detect the fluorescence of T668 and that of M7514 since the wavelength of the fluorescence from T668 is different from that from M7514. In this example, three groups of cell population were detected based on T668 fluorescence as an indicator. As described in the analysis of Example 8, it is known that the high fluorescent cell population exhibiting the highest fluorescent intensity is a cardiomyocyte population and the middle fluorescent population is a non-cardiomyocyte population.

Next, each cell population is separated based on the ratio of fluorescent intensity derived from T668 divided by fluorescent intensity derived from M7514. In the cell population identified as a cardiomyocyte based on T668 signal, cells categorized in the value of more than 150% accounted for 90% of the total number of the cells when the cut off value of 150% of the ratio of T668 fluorescent intensity to M7514 fluorescent intensity was employed; while, in the cell population identified as a non-cardiomyocyte based on T668 signal, cells categorized in the value of more than 150% accounted for 13% of the total number of the cells when the cut off value of 150% of the ratio of T668 fluorescent intensity to M7514 fluorescent intensity was employed. These results demonstrate that the cardiomyocyte has not only the higher content of mitochondria but also the higher transmembrane potential of mitochondria compared to the non-cardiomyocyte.

Example 10

Figures 1, 9:
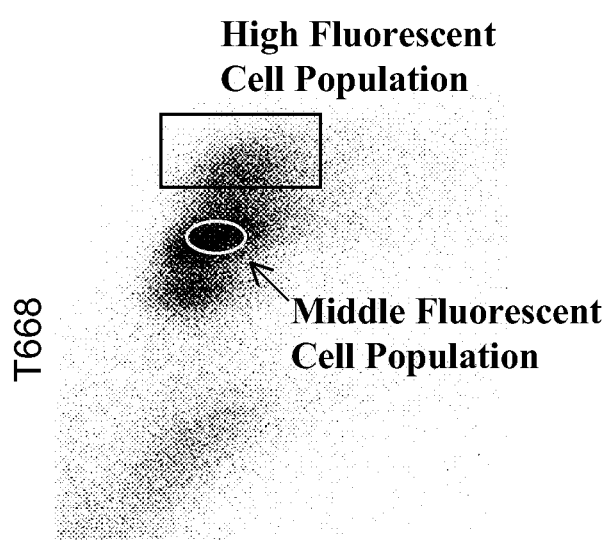

Staining of Fetal Rat Cells Derived from a Whole Heart with a Mitochondrial Indicator T668 and Purification of a Cardiomyocyte Fetal rat heart of 13th day post conception was treated with collagenase and trypsin to collect a cell population. Cells dispersed in the culture medium were exposed to 1 μM (final concentration) of a mitochondrial indicator T668 for 15 minutes at 37° C., washed 3 times, and immediately subjected to FACS analysis. The cells were separated into 3 groups of cell population based on T668 fluorescent intensity (FIG. 9-1). In this example, the high fluorescent cell population exhibiting the highest fluorescent intensity and the middle fluorescent cell population were sorted and cultured.

Then, the cardiomyocyte was identified by immunostaining of the cultured cell using anti-Actinin antibody. In consequence, almost all cells of the cell population with the highest intensity of T668 fluorescent signal consist of the cardiomyocyte and almost all cells of the cell population with the middle fluorescent intensity consist of the non-cardiomyocyte (FIG. 9-2).

Example 11

Figures 1, 10:
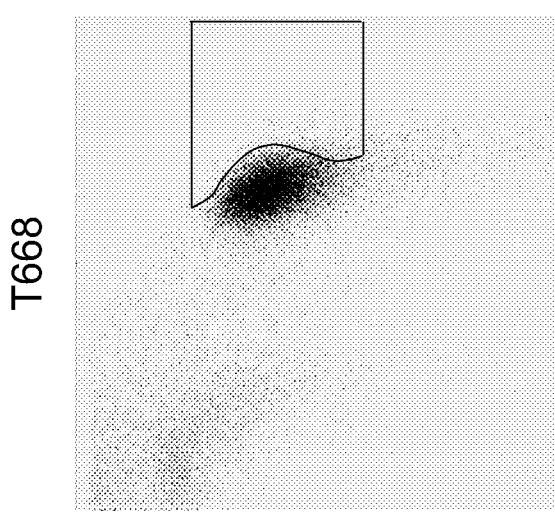
Figures 2, 10:
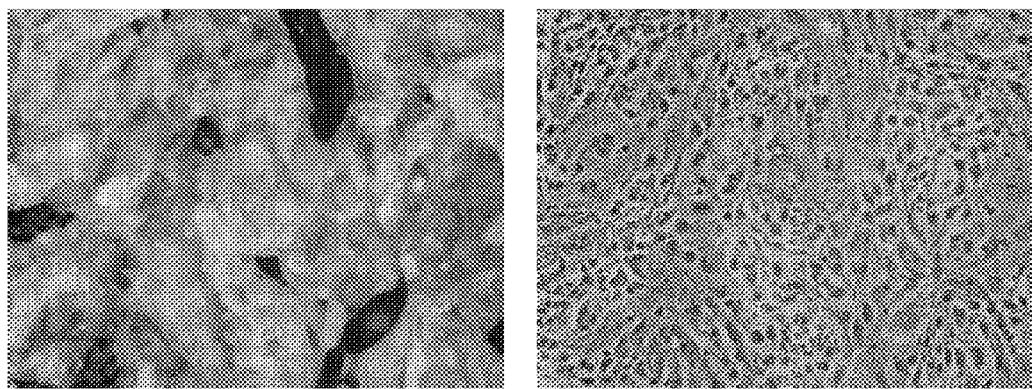

Staining of Whole Fetal Cells with Mitochondrial Indicators T668 and M7512 and Purification of a Cardiomyocyte Fetal rat of 9th day post conception was treated with collagenase and trypsin to collect cell population. Cells dispersed in the culture medium were exposed to 1 µM (final concentration) of a mitochondrial indicator T668 for 15 minutes at 37° C., washed 3 times, and immediately subjected to FACS analysis. One single cell population was mainly observed as a cell population based on the fluorescent intensity. On the other hand, in the high fluorescent intensity area in which the cardiomyocyte was predicted to be detected based on the analysis of a whole heart sample from the later development stage, a definite cell population could not be found (FIG. 10-1). However, since there were a small number of cells exhibiting a higher fluorescent intensity than the main cell population, these cells were collected as a high fluorescent cell population.

The cells were cultured and immunostained with an antibody against a cardiomyocyte marker, Actinin. Approximately more than 95% of cells collected using T668 were found to be a cardiomyocyte (FIG. 10-2). Since the cardiomyocyte is extremely immature in the fetus of 9th day post conception (early embryo), it is considered in the art that quantitative alteration of the mitochondria has not completely occurred. This result demonstrates that, even in such an early stage, it is possible to effectively select the cardiomyocyte using a mitochondrial transmembrane potential as an indicator.

Example 12

Figure 11:
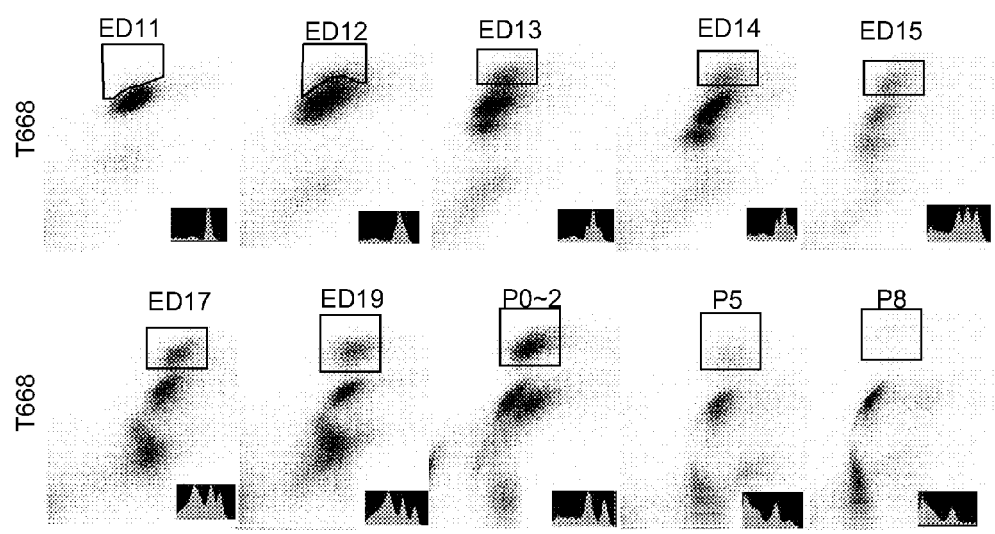
[FIG. 11]

Staining of Rat Cells Derived from a Whole Heart Obtained at 11th Day Post Conception to 8 Days After Birth Using a Mitochondrial Indicator T668 and FACS Analysis Rat heart obtained at 11th day post conception to 8 days after birth was treated with collagenase and trypsin to collect a cell population. Cells dispersed in the culture medium were exposed to 1 µM (final concentration) of a mitochondrial indicator T668 for 15 minutes at 37° C., washed 3 times, and immediately analyzed by FACS. In consequence, the cell population was isolated by T668 fluorescent intensity. High fluorescent cardiomyocyte population exhibiting the highest fluorescent intensity increased in number and cell populations were clearly separated from each other as the development stage progressed (FIG. 11). Therefore, it is shown that it is possible to presume the maturity of the cardiomyocyte by the method provided by the present specification.

Example 13

Figure 12:
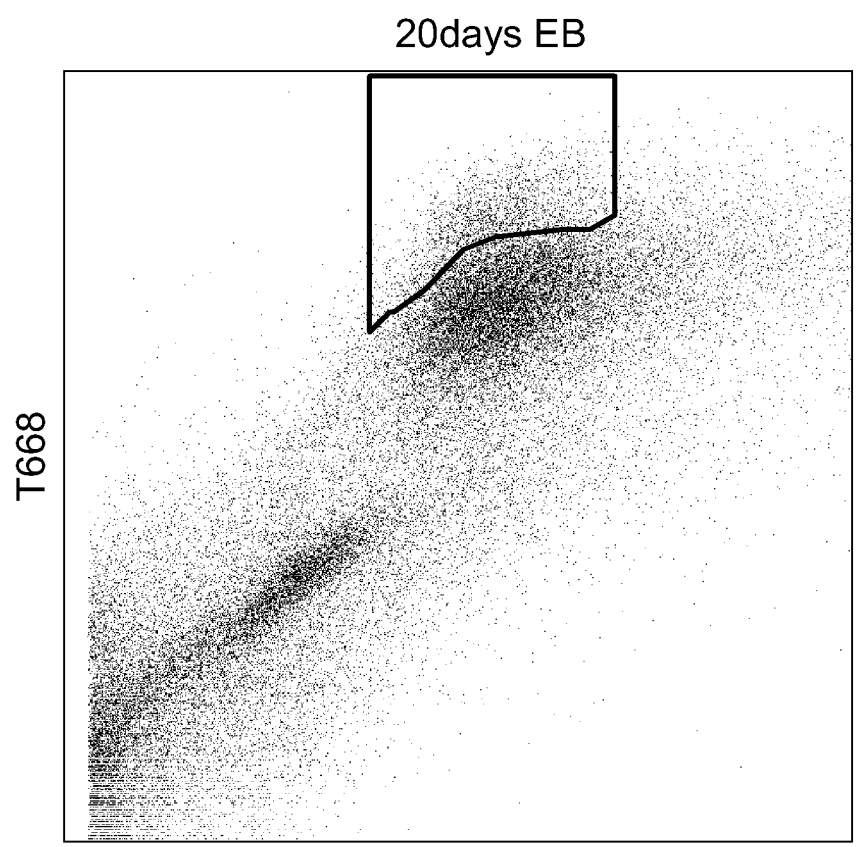
[FIG. 12]

Staining of a Population Consisting of Multiple Types of Cells with a Mitochondrial Indicator T668 and Purification of the Cardiomyocyte ES cells were differentiated into a cell population containing the cardiomyocyte using the same method as that of Example 2. This cell mass composed of multiple types of cells was treated with collagenase and trypsin to obtain discrete cells. Cells dispersed in the culture medium were exposed to 1 µM (final concentration) of a mitochondrial indicator, T668, for 15 minutes at 37° C., washed 3 times, and immediately analyzed by FACS. One single cell population was mainly observed as a cell population based on the fluorescent intensity. On the other hand, in the high fluorescent intensity area in which the cardiomyocyte was predicted to be detected based on the analysis of a whole heart sample from the later development stage, a definite cell population could not be found (FIG. 12). However, since there were a small number of cells exhibiting a higher fluorescent intensity than the main cell population, these cells were collected as a high fluorescent cell population.

The cells were cultured on a large scale and immunostained with an antibody against a cardiomyocyte marker, Actinin. More than 98% of cells collected were found to be a cardiomyocyte. On the other hand, the main cell population was also collected and cultured, followed by immunostaining with an antibody against a cardiomyocyte marker, Actinin. Almost all of the cells collected consist of a non-cardiomyocyte.

Example 14

Staining of Neonatal Rat Cells Derived from a Whole Heart with Mitochondrial Indicator S7563 and Purification of the Cardiomyocyte Neonatal rat heart was treated with collagenase and trypsin to collect a cell population. Cells dispersed in the culture medium were exposed to 1 µM (final concentration) of a mitochondrial indicator S7563 for 15 minutes at 37° C., washed 3 times, and immediately analyzed by FACS. In consequence, the cells were separated into 3 groups of cell population based on S7563 fluorescent intensity. In this example, the high fluorescent cell population exhibiting the highest fluorescent intensity was sorted and cultured.

Then, the cardiomyocyte was identified by immunostaining of the cultured cell using anti-Actinin antibody. In consequence, almost all cells of the cell population with the highest intensity of S7563 fluorescent signal consist of the cardiomyocyte and almost all cells of the cell population with the middle fluorescent population consist of a non-cardiomyocyte.

Industrial Applicability

According to the present invention, it is possible to select a cardiomyocyte from a cardiomyocyte-containing cell mixture without genetic alteration of a cardiomyocyte. Further, according to the present invention, it is also possible to enrich the cardiomyocyte within the cardiomyocyte-containing cell mixture without genetic alteration of the cardiomyocyte and to produce the cardiomyocyte without genetic alteration of the cardiomyocyte. Moreover, it is also possible to evaluate the percentage of the cardiomyocyte in the cardiomyocyte-containing cell mixture prepared by a variety of methods.

According to these embodiments, it is possible to enhance the percentage of the cardiomyocyte in the cardiomyocyte-containing cell mixture and to reduce the various possible side effects against the recipient cardiac tissue (heart) due to the existence of a non-cardiomyocyte upon transplantation.

The invention claimed is:

1. A method of selecting a cardiomyocyte from a cardiomyocyte-containing cell mixture without genetic alteration of the cardiomyocyte comprising selecting the cardiomyocyte on the basis of a relative content of cellular mitochondria and/or a relative mitochondrial transmembrane potential of the cell, wherein said cardiomyocyte-containing cell mixture is a cell mixture derived from a fetus whole heart or a cell mixture derived from a cell having an ability to differentiate to the cardiomyocyte.

2. The method of claim 1, wherein the cardiomyocyte is selected on the basis of a relative content of cellular mitochondria.

3. The method of claim 1, wherein the cardiomyocyte is selected on the basis of a relative mitochondrial transmembrane potential of the cell.

4. The method of claim 1, wherein the cardiomyocyte is selected on the basis of both a relative content of cellular mitochondria and transmembrane potential.

5. The method of claim 1, wherein said method comprises a step of labeling the cardiomyocyte-containing cell mixture with a mitochondrial indicator and a step of measuring a relative content of cellular mitochondria and/or a relative mitochondrial transmembrane potential of the cell.

6. The method of claim 5, wherein said method further comprises a step of culturing the labeled cell in the absence of the mitochondrial indicator, after the step of labeling the cardiomyocyte-containing cell mixture with the mitochondrial indicator, and before the step of measuring a relative content of cellular mitochondria and/or a relative mitochondrial transmembrane potential of the cell.

7. The method of claim 5, wherein said mitochondrial indicator is A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 or T3168.

8. The method of claim 7, wherein said mitochondrial indicator is M7512, T3168, T668 or R302.

9. The method of claim 1, wherein said cardiomyocyte-containing cell mixture is a cell mixture derived from a fetus whole heart.

10. The method of claim 1, wherein said cardiomyocyte-containing cell mixture is a cell mixture derived from a cell having an ability to differentiate to the cardiomyocyte, and the cell having an ability to differentiate to a cardiomyocyte is a stem cell, a progenitor cell or an egg cell.

11. The method of claim 1, further comprising evaluating the ratio of a cardiomyocyte in a cardiomyocyte-containing cell mixture, comprising:
(1) labeling the cardiomyocyte-containing cell mixture with a mitochondrial indicator; and
(2) measuring the ratio of the cardiomyocyte to a non-cardiomyocyte on the basis of a relative content of cellular mitochondria and/or a relative mitochondrial transmembrane potential of the cell, whereby the ratio of a cardiomyocyte in a cardiomyocyte-containing cell mixture can be evaluated.

12. The method of claim 11, wherein said cell having an ability to differentiate to the cardiomyocyte is a stem cell, a progenitor cell, or an egg cell.

13. The method of claim 11, wherein said mitochondrial indicator is A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 or T3168.

14. The method of claim 13, wherein said mitochondrial indicator is M7512, T3168, T668 or R302.

15. A method of enriching a cardiomyocyte from a cardiomyocyte-containing cell mixture without genetic alteration of the cardiomyocyte, comprising:
(1) labeling the cardiomyocyte-containing cell mixture with a mitochondrial indicator; and
(2) selecting the cardiomyocyte on the basis of a relative content of cellular mitochondria and/or a relative mitochondrial transmembrane potential of the cell,
wherein said cardiomyocyte-containing cell mixture is a cell mixture derived from a fetus whole heart or a cell mixture derived from a cell having an ability to differentiate to the cardiomyocyte.

16. The method of claim 15, wherein said cardiomyocyte-containing cell mixture is a cell mixture derived from a fetus whole heart.

17. The method of claim 15, wherein said cardiomyocyte-containing cell mixture is a cell mixture derived from a cell having, an ability to differentiate to the cardiomyocyte. and said cell having an ability to differentiate to a cardiomyocyte is a stem cell, a progenitor cell, or an egg cell.

18. The method of claim 15, wherein said method further comprises a step of culturing the labeled cell in the absence of the mitochondrial indicator, after step (1), and before step (2).

19. The method of claim 15, wherein said mitochondrial indicator is A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 or T3168.

20. The method of claim 19, wherein said mitochondrial indicator is M7512, T3168, T668 or R302.

21. A method of producing a cardiomyocyte without genetic alteration of the cardiomyocyte, comprising:
(1) differentiating and inducing the cardiomyocyte from a cell having an ability to differentiate to the cardiomyocyte to prepare a cardiomyocyte-containing cell mixture;
(2) labeling the cardiomyocyte-containing cell mixture with a mitochondrial indicator; and
(3) selecting the cardiomyocyte on the basis of a relative content of cellular mitochondria and/or a relative mitochondrial transmembrane potential of the cell.

22. The method of claim 21, wherein said cell having an ability to differentiate to the cardiomyocyte is a stem cell, a progenitor cell, or an egg cell.

23. The method of claim 21, wherein said method further comprises a step of culturing the labeled cell in the absence of the mitochondrial indicator, after step (2), before step (3).

24. The method of claim 21, wherein said mitochondrial indicator is A1372, D273, D288, D308, D378, D426, D632, D633, D22421, D23806, L6868, M7502, M7510, M7511, M7512, M7513, M7514, M22422, M22423, M22425, M22426, R302, R634, R648, R14060, R22420, T639, T668, T669 or T3168.

25. The method of claim 24, wherein said mitochondria indicator is M7512, T3168, T668 or R302.

26. A method of isolating a cardiomyocyte from a cardiomyocyte-containing cell mixture without genetic alteration of the cardiomyocyte comprising isolating the cardiomyocyte on the basis of a relative content of cellular mitochondria and/or a relative mitochondrial transmembrane potential of the cell, wherein said cardiomyocyte-containing cell mixture is a cell mixture derived from a fetus whole heart or a cell mixture derived from a cell having an ability to differentiate to the cardiomyocyte.

* * * * *

UNITED STATES PATENT AND TRADEMARK OFFICE
CERTIFICATE OF CORRECTION

PATENT NO. : 8,623,649 B2
APPLICATION NO. : 11/660581
DATED : January 7, 2014
INVENTOR(S) : Fumiyuki Hattori et al.

Page 1 of 1

It is certified that error appears in the above-identified patent and that said Letters Patent is hereby corrected as shown below:

On the Title Page, Item (54) and in the Specification, Column 1, lines 1-4, the Title of the invention should read:

--METHOD OF SELECTING A CARDIOMYOCYTE USING INTRACELLULAR MITOCHONDRIA AS AN INDICATOR.--

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,623,649 B2                                                Page 1 of 1
APPLICATION NO.   : 11/660581
DATED             : January 7, 2014
INVENTOR(S)       : Hattori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1710 days.

Signed and Sealed this
Twenty-second Day of September, 2015

Michelle K. Lee
*Director of the United States Patent and Trademark Office*